(12) United States Patent
Ikari

(10) Patent No.: US 8,399,498 B2
(45) Date of Patent: Mar. 19, 2013

(54) ANIMAL ECTOPARASITE-CONTROLLING AGENT

(75) Inventor: Kaori Ikari, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 19 days.

(21) Appl. No.: 13/194,300

(22) Filed: Jul. 29, 2011

(65) Prior Publication Data

US 2012/0029039 A1    Feb. 2, 2012

(30) Foreign Application Priority Data

Jul. 30, 2010    (JP) ................... 2010-171787

(51) Int. Cl.
  *A01N 43/80*  (2006.01)
  *A01P 7/04*  (2006.01)
  *C07D 261/04*  (2006.01)
(52) U.S. Cl. ........................ 514/378; 548/240
(58) Field of Classification Search .................. 514/378; 548/240
  See application file for complete search history.

(56) References Cited

U.S. PATENT DOCUMENTS

| | | |
|---|---|---|
| 2011/0166358 A1 | 7/2011 | Iwata et al. |
| 2011/0294840 A1 | 12/2011 | Ihara et al. |

FOREIGN PATENT DOCUMENTS

| | | |
|---|---|---|
| EP | 2332927 A1 | 6/2011 |
| JP | 2003-313104 A | 11/2003 |
| WO | WO 2010/032437 A1 | 3/2010 |
| WO | WO 2010/090344 A1 | 8/2010 |

OTHER PUBLICATIONS

Extended European Search Report, dated Dec. 13, 2011, for European Application No. 11175769.6.
Extended European Search Report, dated Nov. 9, 2011, for European Application No. 11175759.7.
Extended European Search Report dated Oct. 21, 2011, for Application No. 11175748.0.
Extended European Search Report dated Oct. 21, 2011, for Application No. 11175750.6.
Georgi et al., Abstract for "Canine Clinical Parasitology," 1991.
Non-Final Office Action for related U.S. Appl. No. 13/194,390, dated Jan. 4, 2013.

*Primary Examiner* — Raymond Henley, III
(74) *Attorney, Agent, or Firm* — Birch, Stewart, Kolasch & Birch, LLP

(57) ABSTRACT

The present invention provides an animal ectoparasite-controlling agent containing as an active ingredient a hydrazide compound represented by the formula (1)

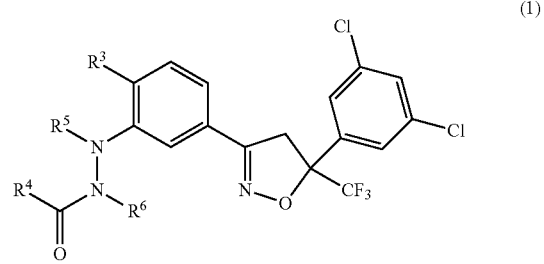

wherein $R^3$ represents a fluorine atom, a chlorine atom, a bromine atom, a methyl group, an ethyl group or a hydrogen atom, $R^5$ and $R^6$ are the same or different each other and each represents a methyl group or a hydrogen atom, $R^4$ represents a C1-C6 alkyl group substituted by a C1-C6 alkoxy group, which shows excellent controlling effects on animal ectoparasites.

16 Claims, No Drawings

ANIMAL ECTOPARASITE-CONTROLLING AGENT

BACKGROUND OF THE INVENTION

The present invention relates to animal ectoparasite-controlling agents and methods for controlling animal ectoparasites.

Heretofore, various compounds for controlling parasites living on the body surface or hair of animals or in the vicinity thereof have been found, and methods for controlling the parasites comprising applying agents containing said compounds to the body surface of animals or orally administrating the agents to animals have been developed (see, for example, Patent literature 1). However, conventional compounds are not always sufficiently effective, and thus there is still a demand for agents comprising compounds having excellent controlling effects on animal ectoparasites.

PRIOR ART REFERENCE

Patent Literature

Patent literature 1: JP-A-2003-313104

SUMMARY OF THE INVENTION

The object of the present invention is to provide an animal ectoparasite-controlling agent having an excellent controlling effect.

The inventors of the present invention have intensively studied for attaining the above object, and finally found that an agent containing a hydrazide compound represented by the following formula (1) as an active ingredient shows excellent controlling effects on animal ectoparasites, thereby reaching the present invention.

Namely, the present invention includes the followings:

[1] An animal ectoparasite-controlling agent comprising a hydrazide compound represented by the formula (1):

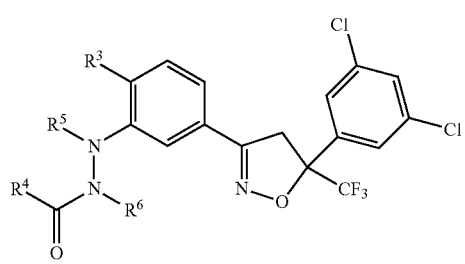

wherein $R^3$ represents a fluorine atom, a chlorine atom, a bromine atom, a methyl group, an ethyl group or a hydrogen atom, $R^5$ and $R^6$ are the same or different from each other and each represents a methyl group or a hydrogen atom, and $R^4$ represents a C1-C6 alkyl group substituted by a C1-C6 alkoxy group (hereinafter referred to as "the present hydrazide compound"), as an active ingredient (hereinafter referred to as "the controlling agent of the present invention").

[2] The animal ectoparasite-controlling agent according to the item [1], wherein in the formula (1) $R^6$ is a hydrogen atom.

[3] The animal ectoparasite-controlling agent according to the item [1] or [2], wherein in the formula (1) $R^3$ is a chlorine atom.

[4] The animal ectoparasite-controlling agent according to any one of the items [1] to [3], wherein in the formula (1) $R^5$ is a hydrogen atom.

[5] The animal ectoparasite-controlling agent according to any one of the items [1] to [3], wherein in the formula (1) $R^5$ is a methyl group.

[6] The animal ectoparasite-controlling agent according to any one of the items [1] to [5], which is in the form of an oral formulation or an external formulation for skin.

[7] The animal ectoparasite-controlling agent according to any one of the items [1] to [5], which is in the form of a liquid formulation.

[8] The animal ectoparasite-controlling agent according to any one of the items [1] to [5], which is in the form of a capsule formulation, a tablet or a chewable tablet.

[9] The animal ectoparasite-controlling agent according to any one of the items [1] to [8], wherein the animal ectoparasite is a flea or a tick.

[10] A method for controlling an animal ectoparasite, which comprises applying an effective amount of a hydrazide compound of the formula (1):

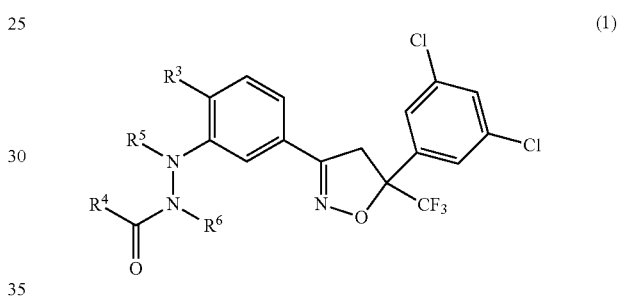

wherein $R^3$ represents a fluorine atom, a chlorine atom, a bromine atom, a methyl group, an ethyl group or a hydrogen atom, $R^5$ and $R^6$ are the same or different from each other and each represents a methyl group or a hydrogen atom, and $R^4$ represents a C1-C6 alkyl group substituted by a C1-C6 alkoxy group, to an animal.

[11] The method for controlling an animal ectoparasite according to the item [10], wherein the hydrazide compound is orally administered.

[12] The method for controlling an animal ectoparasite according to the item [10], wherein the hydrazide compound is externally applied to a skin.

[13] The method for controlling an animal ectoparasite according to the item [12], wherein the hydrazide compound is applied by spot-on application or pour-on application.

[14] The method for controlling an animal ectoparasite according to any one of the items [10] to [13], wherein the animal is a dog or a cat.

[15] The method for controlling an animal ectoparasite according to any one of the items [10] to [13], wherein the animal is a cow, a horse, a pig or a sheep.

[16] The method for controlling an animal ectoparasite according to any one of the items [10] to [15], wherein the animal ectoparasite is a flea or a tick.

EFFECT OF THE INVENTION

The controlling agent of the present invention has excellent controlling effects on animal ectoparasites.

DETAILED DESCRIPTION OF THE EMBODIMENTS

Examples of the "C1-C6 alkoxy group" used herein include a methoxy group, an ethoxy group, a propoxy group, an isopropoxy group, a butoxy group, an isobutoxy group, a sec-butoxy group, a tert-butoxy group, a pentyloxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxy group, a hexyloxy group, a 1-methylpentyloxy group, a 2-methylpentyloxy group, a 1,1-dimethylbutoxy group and a 1,3-dimethylbutoxy group.

Examples of the "C1-C6 alkyl group" used herein include a methyl group, an ethyl group, a propyl group, an isopropyl group, a butyl group, an isobutyl group, a sec-butyl group, a tert-butyl group, a pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a hexyl group, a 1-methylpentyl group, a 2-methylpentyl group, a 1,1-dimethylbutyl group and a 1,3-dimethylbutyl group.

Examples of the present hydrazide compound include the following hydrazide compounds:

hydrazide compounds represented by the formula (1), wherein $R^3$ is a methyl group, an ethyl group, a fluorine atom, a chlorine atom or a bromine atom;

hydrazide compounds represented by the formula (1), wherein $R^3$ is a fluorine atom, a chlorine atom or a bromine atom;

hydrazide compounds represented by the formula (1), wherein $R^3$ is a hydrogen atom;

hydrazide compounds represented by the formula (1), wherein $R^3$ is a methyl group; hydrazide compounds represented by the formula (1), wherein $R^3$ is an ethyl group;

hydrazide compounds represented by the formula (1), wherein $R^3$ is a fluorine atom;

hydrazide compounds represented by the formula (1), wherein $R^3$ is a chlorine atom;

hydrazide compounds represented by the formula (1), wherein $R^3$ is a bromine atom;

hydrazide compounds represented by the formula (1), wherein $R^4$ is a methyl group substituted by a C1-C6 alkoxy group;

hydrazide compounds represented by the formula (1), wherein $R^4$ is a methyl group substituted by a C1-C4 alkoxy group;

hydrazide compounds represented by the formula (1), wherein $R^4$ is a methoxymethyl group;

hydrazide compounds represented by the formula (1), wherein $R^4$ an ethoxymethyl group;

hydrazide compounds represented by the formula (1), wherein $R^5$ is a hydrogen atom;

hydrazide compounds represented by the formula (1), wherein $R^5$ is a methyl group;

hydrazide compounds represented by the formula (1), wherein $R^6$ is a hydrogen atom;

hydrazide compounds represented by the formula (1), wherein $R^6$ is a methyl group;

hydrazide compounds represented by the formula (1), wherein $R^5$ is a hydrogen atom, and $R^6$ is a hydrogen atom;

hydrazide compounds represented by the formula (1), wherein $R^5$ is a hydrogen atom, and $R^6$ is a methyl group;

hydrazide compounds represented by the formula (1), wherein $R^5$ is a methyl group, and $R^6$ is a hydrogen atom;

hydrazide compounds represented by the formula (1), wherein $R^5$ is a methyl group, and $R^6$ is a methyl group;

hydrazide compounds represented by the formula (1), wherein $R^3$ is a fluorine atom, a chlorine atom or a bromine atom, and $R^5$ is a hydrogen atom;

hydrazide compounds represented by the formula (1), wherein $R^3$ is a chlorine atom, and $R^5$ is a hydrogen atom;

hydrazide compounds represented by the formula (1), wherein $R^3$ is a fluorine atom, a chlorine atom or a bromine atom, and $R^5$ is a methyl group;

hydrazide compounds represented by the formula (1), wherein $R^3$ is a chlorine atom, and $R^5$ is a methyl group;

hydrazide compounds represented by the formula (1), wherein $R^3$ is a fluorine atom, a chlorine atom or a bromine atom, and $R^6$ is a methyl group;

hydrazide compounds represented by the formula (1), wherein $R^3$ is a chlorine atom, and $R^6$ is a hydrogen atom;

hydrazide compounds represented by the formula (1), wherein $R^3$ is a chlorine atom, and $R^6$ is a methyl group;

hydrazide compounds represented by the formula (1), wherein $R^3$ is a fluorine atom, a chlorine atom or a bromine atom, $R^5$ is a hydrogen atom, and $R^6$ is a hydrogen atom;

hydrazide compounds represented by the formula (1), wherein $R^3$ is a hydrogen atom, $R^5$ is a hydrogen atom, and $R^6$ is a hydrogen atom;

hydrazide compounds represented by the formula (1), wherein $R^3$ is a methyl group, $R^5$ is a hydrogen atom, and $R^6$ is a hydrogen atom;

hydrazide compounds represented by the formula (1), wherein $R^3$ is an ethyl group, $R^5$ is a hydrogen atom, and $R^6$ is a hydrogen atom;

hydrazide compounds represented by the formula (1), wherein $R^3$ is a fluorine atom, $R^5$ is a hydrogen atom, and $R^6$ is a hydrogen atom;

hydrazide compounds represented by the formula (1), wherein $R^3$ is a chlorine atom, $R^5$ is a hydrogen atom, and $R^6$ is a hydrogen atom;

hydrazide compounds represented by the formula (1), wherein $R^3$ is a bromine atom, $R^5$ is a hydrogen atom, and $R^6$ is a hydrogen atom;

hydrazide compounds represented by the formula (1), wherein $R^3$ is a fluorine atom, a chlorine atom or a bromine atom, $R^5$ is a methyl group, and $R^6$ is a hydrogen atom;

hydrazide compounds represented by the formula (1), wherein $R^3$ is a hydrogen atom, $R^5$ is a methyl group, and $R^6$ is a hydrogen atom;

hydrazide compounds represented by the formula (1), wherein $R^3$ is a methyl group, $R^5$ is a methyl group, and $R^6$ is a hydrogen atom;

hydrazide compounds represented by the formula (1), wherein $R^3$ is an ethyl group, $R^5$ is a methyl group, and $R^6$ is a hydrogen atom;

hydrazide compounds represented by the formula (1), wherein $R^3$ is a fluorine atom, $R^5$ is a methyl group, and $R^6$ is a hydrogen atom;

hydrazide compounds represented by the formula (1), wherein $R^3$ is a chlorine atom, $R^5$ is a methyl group, and $R^6$ is a hydrogen atom;

hydrazide compounds represented by the formula (1), wherein $R^3$ is a bromine atom, $R^5$ is a methyl group, and $R^6$ is a hydrogen atom;

hydrazide compounds represented by the formula (1), wherein $R^3$ is a hydrogen atom, $R^5$ is a hydrogen atom, and $R^6$ is a methyl group;

hydrazide compounds represented by the formula (1), wherein $R^3$ is a methyl group, $R^5$ is a hydrogen atom, and $R^6$ is a methyl group;

hydrazide compounds represented by the formula (1), wherein $R^3$ is an ethyl group, $R^5$ is a hydrogen atom, and $R^6$ is a methyl group;

hydrazide compounds represented by the formula (1), wherein $R^3$ is a fluorine atom, $R^5$ is a hydrogen atom, and $R^6$ is a methyl group;

hydrazide compounds represented by the formula (1), wherein $R^3$ is a chlorine atom, $R^5$ is a hydrogen atom, and $R^6$ is a methyl group;

hydrazide compounds represented by the formula (1), wherein $R^3$ is a bromine atom, $R^5$ is a hydrogen atom, and $R^6$ is a methyl group;

hydrazide compounds represented by the formula (1), wherein $R^3$ is a hydrogen atom, $R^5$ is a methyl group, and $R^6$ is a methyl group;

hydrazide compounds represented by the formula (1), wherein $R^3$ is a methyl group, $R^5$ is a methyl group, and $R^6$ is a methyl group;

hydrazide compounds represented by the formula (1), wherein $R^3$ is an ethyl group, $R^5$ is a methyl group, and $R^6$ is a methyl group;

hydrazide compounds represented by the formula (1), wherein $R^3$ is a fluorine atom, $R^5$ is a methyl group, and $R^6$ is a methyl group;

hydrazide compounds represented by the formula (1), wherein $R^3$ is a chlorine atom, $R^5$ is a methyl group, and $R^6$ is a methyl group;

hydrazide compounds represented by the formula (1), wherein $R^3$ is a bromine atom, $R^5$ is a methyl group, and $R^6$ is a methyl group;

hydrazide compounds represented by the formula (1), wherein $R^4$ is a methyl group substituted by a C1-C6 alkoxy group, and $R^5$ is a hydrogen atom;

hydrazide compounds represented by the formula (1), wherein $R^4$ is a methyl group substituted by a C1-C6 alkoxy group, and $R^5$ is a methyl group;

hydrazide compounds represented by the formula (1), wherein $R^4$ is a methyl group substituted by a C1-C6 alkoxy group, and $R^6$ is a hydrogen atom;

hydrazide compounds represented by the formula (1), wherein $R^4$ is a methyl group substituted by a C1-C6 alkoxy group, and $R^6$ is a methyl group;

hydrazide compounds represented by the formula (1), wherein $R^4$ is a methyl group substituted by a C1-C6 alkoxy group, $R^5$ is a hydrogen atom, and $R^6$ is a hydrogen atom;

hydrazide compounds represented by the formula (1), wherein $R^4$ is a methyl group substituted by a C1-C6 alkoxy group, $R^5$ is a methyl group, and $R^6$ is a hydrogen atom;

hydrazide compounds represented by the formula (1), wherein $R^4$ is a methyl group substituted by a C1-C6 alkoxy group, $R^5$ is a hydrogen atom, and $R^6$ is a methyl group;

hydrazide compounds represented by the formula (1), wherein $R^4$ is a methyl group substituted by a C1-C6 alkoxy group, $R^5$ is a methyl group, and $R^6$ is a methyl group;

hydrazide compounds represented by the formula (1), wherein $R^4$ is a methoxymethyl group, and $R^5$ is a hydrogen atom;

hydrazide compounds represented by the formula (1), wherein $R^4$ is a methoxymethyl group, and $R^5$ is a methyl group;

hydrazide compounds represented by the formula (1), wherein $R^4$ is a methoxymethyl group, and $R^6$ is a hydrogen atom;

hydrazide compounds represented by the formula (1), wherein $R^4$ is a methoxymethyl group, and $R^6$ is a methyl group;

hydrazide compounds represented by the formula (1), wherein $R^4$ is a methoxymethyl group, $R^5$ is a hydrogen atom, and $R^6$ is a hydrogen atom;

hydrazide compounds represented by the formula (1), wherein $R^4$ is a methoxymethyl group, $R^5$ is a methyl group, and $R^6$ is a hydrogen atom;

hydrazide compounds represented by the formula (1), wherein $R^4$ is a methoxymethyl group, $R^5$ is a hydrogen atom, and $R^6$ is a methyl group;

hydrazide compounds represented by the formula (1), wherein $R^4$ is a methoxymethyl group, $R^5$ is a methyl group, and $R^6$ is a methyl group;

hydrazide compounds represented by the formula (1), wherein $R^3$ is a fluorine atom, a chlorine atom or a bromine atom, and $R^4$ is a methyl group substituted by a C1-C6 alkoxy group;

hydrazide compounds represented by the formula (1), wherein $R^3$ is a chlorine atom, and $R^4$ is a methyl group substituted by a C1-C6 alkoxy group;

hydrazide compounds represented by the formula (1), wherein $R^3$ is a fluorine atom, a chlorine atom or a bromine atom, $R^4$ is a methyl group substituted by a C1-C6 alkoxy group, and $R^5$ is a hydrogen atom;

hydrazide compounds represented by the formula (1), wherein $R^3$ is a chlorine atom, $R^4$ is a methyl group substituted by a C1-C6 alkoxy group, and $R^5$ is a hydrogen atom;

hydrazide compounds represented by the formula (1), wherein $R^3$ is a fluorine atom, a chlorine atom or a bromine atom, $R^4$ is a methyl group substituted by a C1-C6 alkoxy group, and $R^5$ is a methyl group;

hydrazide compounds represented by the formula (1), wherein $R^3$ is a chlorine atom, $R^4$ is a methyl group substituted by a C1-C6 alkoxy group, and $R^5$ is a methyl group;

hydrazide compounds represented by the formula (1), wherein $R^3$ is a fluorine atom, a chlorine atom or a bromine atom, $R^4$ is a methyl group substituted by a C1-C6 alkoxy group, and $R^6$ is a hydrogen atom;

hydrazide compounds represented by the formula (1), wherein $R^3$ is a chlorine atom, $R^4$ is a methyl group substituted by a C1-C6 alkoxy group, and $R^6$ is a hydrogen atom;

hydrazide compounds represented by the formula (1), wherein $R^3$ is a chlorine atom, $R^4$ is a methyl group substituted by a C1-C6 alkoxy group, and $R^6$ is a methyl group;

hydrazide compounds represented by the formula (1), wherein $R^3$ is a fluorine atom, a chlorine atom or a bromine atom, $R^4$ is a methyl group substituted by a C1-C6 alkoxy group, $R^5$ is a hydrogen atom, and $R^6$ is a hydrogen atom;

hydrazide compounds represented by the formula (1), wherein $R^3$ is a chlorine atom, $R^4$ is a methyl group substituted by a C1-C6 alkoxy group, $R^5$ is a hydrogen atom, and $R^6$ is a hydrogen atom;

hydrazide compounds represented by the formula (1), wherein $R^3$ is a fluorine atom, a chlorine atom or a bromine atom, $R^4$ is a methyl group substituted by a C1-C6 alkoxy group, $R^5$ is a methyl group, and $R^6$ is a hydrogen atom;

hydrazide compounds represented by the formula (1), wherein $R^3$ is a chlorine atom, $R^4$ is a methyl group substituted by a C1-C6 alkoxy group, $R^5$ is a methyl group, and $R^6$ is a hydrogen atom;

hydrazide compounds represented by the formula (1), wherein $R^3$ is a chlorine atom, $R^4$ is a methyl group substituted by a C1-C6 alkoxy group, $R^5$ is a hydrogen atom, and $R^6$ is a methyl group;

hydrazide compounds represented by the formula (1), wherein $R^3$ is a chlorine atom, $R^4$ is a methyl group substituted by a C1-C6 alkoxy group, $R^5$ is a methyl group, and $R^6$ is a methyl group.

Hereinafter, methods for producing the present hydrazide compound will be explained:

The present hydrazide compound can be produced, for example, by the following Production methods 1 to 3.

Production Method 1:

The present hydrazide compound can be produced by reacting the compound (2) with the compound (3):

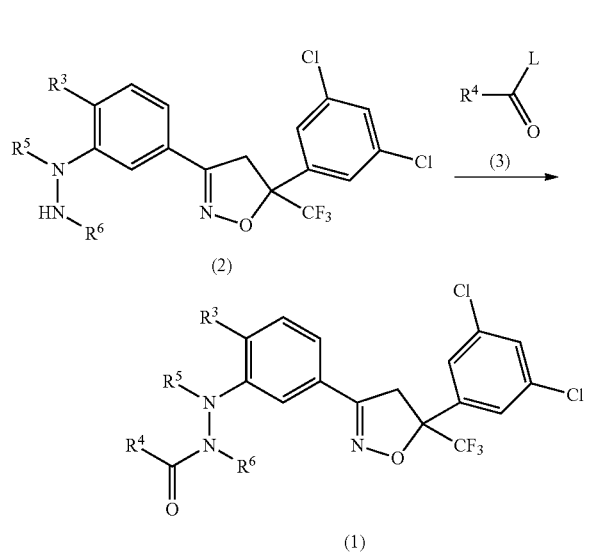

wherein $R^3$, $R^4$, $R^5$ and $R^6$ are as defined above and L represents a hydroxyl group or a chlorine atom.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide; sulfolane; halogenated hydrocarbons such as 1,2-dichloroethane, chloroform and chlorobenzene; and their mixtures.

When L is a chlorine atom, the reaction is generally performed in the presence of a base.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

When L is a hydroxyl group, the reaction is performed in the presence of a condensation agent.

Examples of the condensation agent to be used in the reaction include dicyclohexylcarbodiimide and 1-(3-dimethylaminopropyl)-3-ethyl carbodiimide hydrochloride.

In the reaction, the amount of the compound (3) to be used is generally 1 to 10 mol relative to 1 mol of the compound (2), and the amount of the base or the condensation agent to be used is generally 1 to 10 mol relative to 1 mol of the compound (2).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the present hydrazide compound. The isolated present hydrazide compound may be further purified, for example, by chromatography, recrystallization or the like.

Production Method 2:

The present hydrazide compound can be produced by reacting the compound (4) with the compound (5):

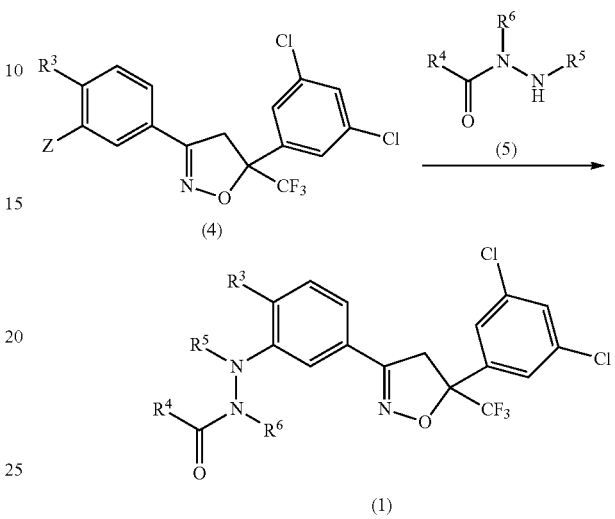

wherein $R^3$, $R^4$, $R^5$ and $R^6$ are as defined above and Z represents an elimination group such as a fluorine atom, a chlorine atom, a bromine atom, an iodine atom, a methanesulfonyloxy group, a p-toluenesulfonyloxy group and a trifluoromethanesulfonyloxy group.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide; sulfolane; halogenated hydrocarbons such as 1,2-dichloroethane, chloroform and chlorobenzene; and their mixtures.

The reaction is optionally performed in the presence of a base.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

In the reaction, the amount of the compound (5) to be used is generally 1 to 5 mol relative to 1 mol of the compound (4), and the amount of the base to be used is generally 1 to 5 mol relative to 1 mol of the compound (4).

The reaction temperature is generally within a range of 0 to 100° C., and the reaction time is generally within a range of 0.1 to 24 hours.

After the reaction is completed, the reaction mixture may be worked up, for example, by extraction with an organic solvent, drying and concentration, to isolate the present hydrazide compound. The isolated present hydrazide compound may be further purified, for example, by chromatography, recrystallization or the like.

In addition, the reaction can be performed by a coupling reaction with a common transition metal catalyst as described in the references.

Production Method 3

The present hydrazide compound can be produced by reacting the compound (2) with the compound (21):

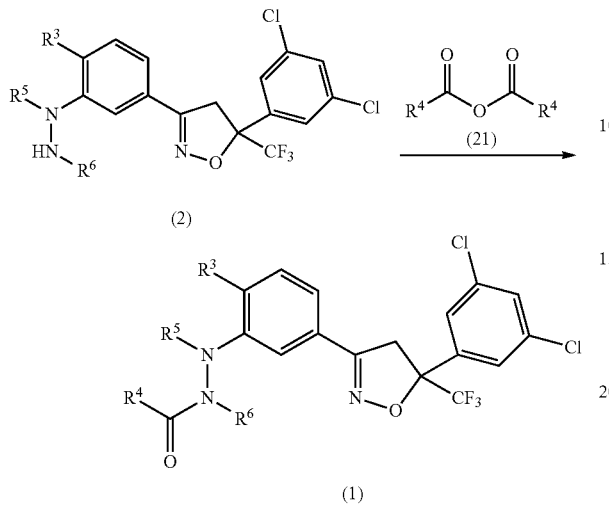

wherein $R^3$, $R^4$, $R^5$ and $R^6$ are as defined above.

The reaction is optionally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide; sulfolane; halogenated hydrocarbons such as 1,2-dichloroethane, chloroform and chlorobenzene; and their mixtures.

The reaction is optionally performed in the presence of a base.

Examples of the base to be used in the reaction include alkali metal hydrides such as sodium hydride; carbonates such as potassium carbonate; alkali metal alkoxides such as potassium tert-butoxide; and organic amines such as triethylamine, pyridine, 4-(dimethyl amino)pyridine and imidazole.

In the above reaction, the amount of the compound (21) to be used is generally 1 to 10 mol relative to 1 mol of the compound (2), and if appropriate, may be used as a solvent. If the above base is needed, the amount of the base is generally 1 to 10 mol relative to 1 mol of the compound (2).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the present hydrazide compound. The isolated present hydrazide compound may be further purified, for example, by chromatography, recrystallization or the like.

Hereinafter, methods for producing the intermediates to be used for the production of the present hydrazide compound will be described:

Reference Production Method 1:

The compound (2) wherein $R^6$ is a hydrogen atom, i.e. the compound (2-1), can be produced by reacting the compound (6) with the nitrous acid compound (7), and then reacting the reaction mixture with the reductant (8).

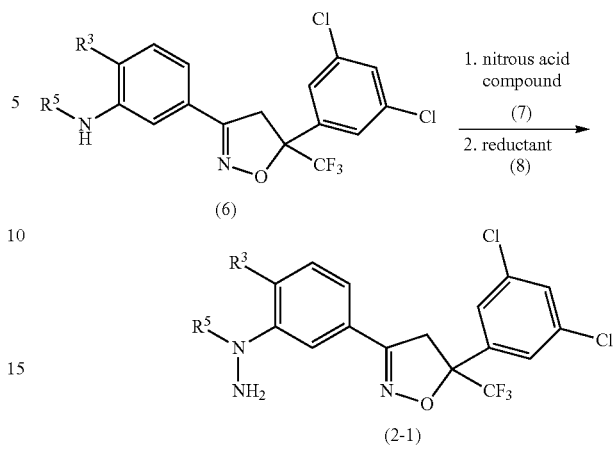

wherein $R^3$ and $R^5$ are as defined above.

The reaction is generally performed in a solvent.

Examples of the solvent to be used in the reaction include water; ethers such as tetrahydrofuran, diethyl ether, tert-butyl methyl ether, ethylene glycol dimethyl ether and 1,4-dioxane; acid amides such as N,N-dimethylformamide; aromatic hydrocarbons such as toluene and xylene; sulfoxides such as dimethyl sulfoxide; sulfolane; halogenated hydrocarbons such as 1,2-dichloroethane, chloroform and chlorobenzene; and their mixtures.

Examples of the nitrous acid compound (7) to be used in the reaction include salts of nitrous acid such as sodium nitrite and esters of nitrous acid such as ethyl nitrite.

Examples of the reductant (8) to be used in the reaction include salts of sulfurous acid such as sodium sulfite; metals such as zinc; and tin(II) chloride.

In the above reaction, the amount of the nitrous acid compound (7) to be used is generally 1 to 10 mol relative to 1 mol of the compound (6), and the amount of the reductant (8) is generally 1 to 10 mol relative to 1 mol of the compound (6).

The reaction temperature in the reaction of the compound (6) with the nitrous acid compound (7) is generally within a range of −20 to 30° C., and the reaction time is generally within a range of 0.5 to 24 hours.

The reaction mixture obtained by the reaction of the compound (6) with the nitrous acid compound (7) may be directly employed in the reaction with the reductant (8). The reaction temperature in the reaction is generally within a range of −20° C. to 50° C., and the reaction time is generally up to 24 hours.

After the reaction is completed, the reaction mixture may be worked up, for example, by extraction with an organic solvent, drying and concentration, to isolate the compound (2-1). The isolated compound (2-1) may be further purified, for example, by chromatography, recrystallization or the like.

Reference Production Method 2:

The compound (2) wherein $R^6$ is a hydrogen atom, i.e. the compound (2-1), can be also produced by reacting the compound (6) with an amination agent (9).

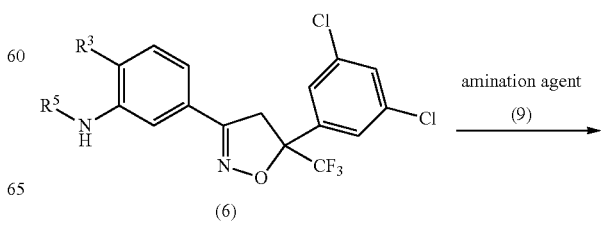

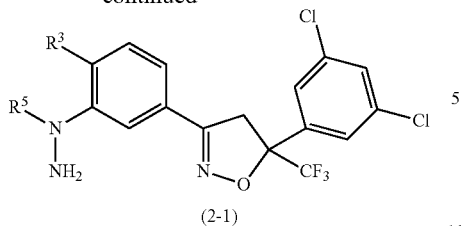

(2-1)

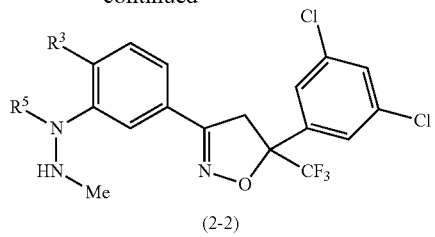

(2-2)

wherein $R^3$ and $R^5$ are as defined above.

The reaction is generally performed in a solvent.

Examples of the solvent to be used in the reaction include water; ethers such as tetrahydrofuran, diethyl ether, tert-butyl methyl ether, ethylene glycol dimethyl ether and 1,4-dioxane; acid amides such as N,N-dimethylformamide; aromatic hydrocarbons such as toluene and xylene; sulfoxides such as dimethyl sulfoxide; sulfolane; halogenated hydrocarbons such as 1,2-dichloroethane, chloroform and chlorobenzene; and their mixtures.

The reaction is generally performed in the presence of a base.

Examples of the base to be used in the reaction include alkali metal hydrides such as sodium hydride; carbonates such as potassium carbonate; alkali metal alkoxides such as potassium tert-butoxide; metal hydroxides such as sodium hydroxide; and organic amines such as triethylamine and pyridine.

Examples of the amination agent (9) to be used in the reaction include chloramines such as chloramine; O-acyl hydroxylamines such as O-mesitoyl hydroxylamine; O-sulfonyl hydroxylamines; and hydroxylamine-O-sulfonic acid.

In the reaction, the amination agent (9) can be generated in the reaction system. For example, when chloramine is used as the amination agent (9), sodium hypochlorite and ammonia as starting materials may be mixed together in the reaction system to generate chloramine.

In the reaction, the amount of the amination agent (9) to be used is generally 1 to 10 mol relative to 1 mol of the compound (6), and the amount of the base to be used is generally 1 to 10 mol relative to 1 mol of the compound (6).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the compound (2-1). The isolated compound (2-1) may be further purified, for example, by chromatography, recrystallization or the like.

Reference Production Method 3:

The compound (2) wherein $R^6$ is a methyl group, i.e. the compound (2-2), can be produced by reacting the compound (2-1) with the compound (10).

wherein $R^3$, $R^5$ and Z are as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide; sulfolane; halogenated hydrocarbons such as 1,2-dichloroethane, chloroform and chlorobenzene; and their mixtures.

The reaction is generally performed in the presence of a base.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

In the reaction, the amount of the compound (10) to be used is generally 1 to 10 mol relative to 1 mol of the compound (2-1), and the amount of the base to be used is generally 1 to 10 mol relative to 1 mol of the compound (2-1).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the compound (2-2). The isolated compound (2-2) may be further purified, for example, by chromatography, recrystallization or the like.

Reference Production Method 4:

The compound (6) wherein $R^5$ is a hydrogen atom, i.e. the compound (6-1), can be produced by reducing the compound (11) according to any one of the following methods (i) to (iii):

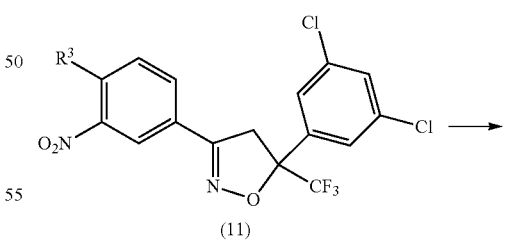

(11)

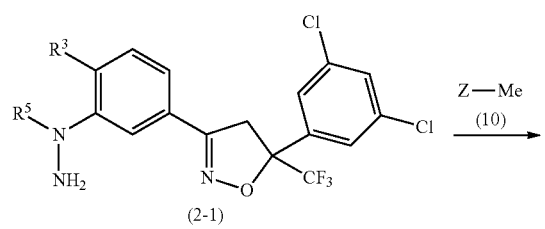

(2-1)

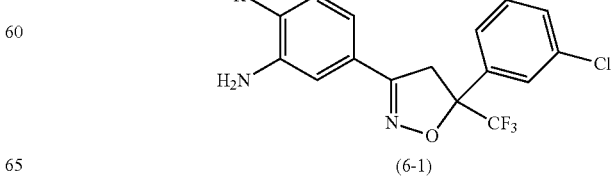

(6-1)

wherein R³ is as defined above.

(i) Reaction with a Hydrogen Gas in the Presence of a Transition Metal Catalyst:

The reaction is performed in a solvent.

Examples of the solvent to be used in the reaction include esters such as ethyl acetate; alcohols such as ethanol and methanol; water; acetic acid; hydrochloric acid; and these mixtures.

Examples of the transition metal catalyst to be used in the reaction include Raney nickel, palladium-carbon and platinum dioxide and the like.

In the reaction, the amount of the transition metal catalyst to be used is generally 0.01 to 0.5 mol relative to 1 mol of the compound (11).

The amount of the hydrogen gas to be used is generally 1 to 100 mol relative to 1 mol of the compound (11).

The reaction temperature is generally within a range of 0 to 80° C., and the reaction time is generally within a range of 0.1 to 24 hours.

After the reaction is completed, the reaction mixture may be filtered, and if necessary, worked up, for example, by extraction with an organic solvent, drying and concentration, to isolate the compound (6-1). The isolated compound (6-1) may be further purified, for example, by chromatography, recrystallization or the like.

(ii) Reaction with a Hydrazine in the Presence of a Base:

The reaction is performed in a solvent.

Examples of the solvent to be used in the reaction include ethers such as diethylene glycol and triethylene glycol; water; and their mixtures.

Examples of the base to be used in the reaction include alkali metal hydroxides such as potassium hydroxide.

Examples of the hydrazine to be used in the reaction include hydrazine hydrate.

In the reaction, the amount of the base to be used is generally 1 to 10 mol relative to 1 mol of the compound (11), and the amount of the hydrazine to be used is generally 1 to 10 mol relative to 1 mol of the compound (11).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the compound (6-1). The isolated compound (6-1) may be further purified, for example, by chromatography, recrystallization or the like.

(iii) Reaction with a Metal in the Presence of an Acid:

The reaction is generally performed in a solvent.

Examples of the solvent to be used in the reaction include alcohols such as ethanol; water; and their mixtures.

Examples of the metal to be used in the reaction include iron, tin and tin(II) chloride.

Examples of the acid to be used in the reaction include acetic acid, hydrochloric acid and sulfuric acid.

In the reaction, the amount of the metal to be used is generally 2 to 20 mol relative to 1 mol of the compound (11), and the amount of the acid to be used is generally 0.1 to 10 mol relative to 1 mol of the compound (11).

The reaction temperature is generally within a range of 0 to 100° C., and the reaction time is generally within a range of 0.5 to 12 hours.

After the reaction is completed, the reaction mixture may be filtered, and if necessary, worked up, for example, by extraction with an organic solvent, drying and concentration, to isolate the compound (6-1). The isolated compound (6-1) may be further purified, for example, by chromatography, recrystallization or the like.

Reference Production Method 5:

The compound (6) wherein $R^5$ is a methyl group, i.e. the compound (6-2), can be produced by reacting the compound (6-1) with the compound (10).

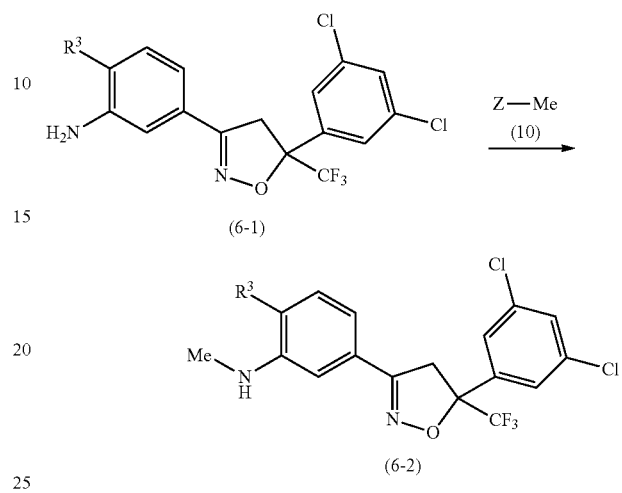

wherein $R^3$ and Z are as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide; sulfolane; halogenated hydrocarbons such as 1,2-dichloroethane, chloroform and chlorobenzene; and their mixtures.

The reaction is generally performed in the presence of a base.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

In the reaction, the amount of the compound (10) to be used is generally 1 to 10 mol relative to 1 mol of the compound (6-1), and the amount of the base to be used is generally 1 to 10 mol relative to 1 mol of the compound (6-1).

The reaction temperature is generally within a range of 0 to 100° C., and the reaction time is generally within a range of 0.5 to 24 hours.

After the reaction is completed, the reaction mixture may be worked up, for example, by extraction with an organic solvent, drying and concentration, to isolate the compound (6-2). The isolated compound (6-2) may be further purified, for example, by chromatography, recrystallization or the like.

Reference Production Method 6:

The compound (11) can be produced by reacting the compound (13) with a base, and then reacting the reaction mixture with the compound (14).

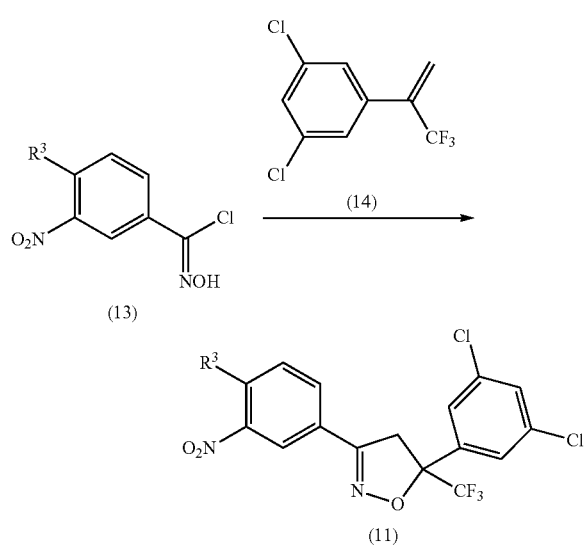

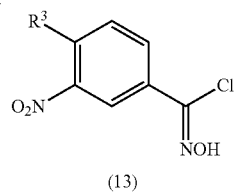

wherein R³ is as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; hydrocarbons such as toluene; esters such as ethyl acetate; acid amides such as N,N-dimethylformamide; nitriles such as acetonitrile; sulfoxides such as dimethyl sulfoxide; and their mixtures.

Examples of the chlorination agent (16) to be used in the reaction include a chlorine gas and N-chlorosuccinimide.

In the above reaction, the amount of the chlorination agent (16) to be used is generally 1 to 10 mol relative to 1 mol of the compound (15).

The reaction temperature in the reaction is generally within a range of −20° C. to 80° C., and the reaction time is generally within a range of 0.5 to 24 hours.

After the reaction is completed, the reaction mixture may be worked up, for example, by extraction with an organic solvent, drying and concentration, to isolate the compound (13). The isolated compound (13) may be further purified, for example, by chromatography, recrystallization or the like.

Reference Production Method 8:

The compound (15) can be produced by reacting the compound (17) with hydroxylamine.

wherein R³ is as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene; esters such as ethyl acetate; sulfoxides such as dimethyl sulfoxide; and their mixtures.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

In the reaction, the amount of the compound (14) to be used is generally 1 to 10 mol relative to 1 mol of the compound (13), and the amount of the base to be used is generally 1 to 10 mol relative to 1 mol of the compound (13).

The reaction temperature in the reaction of the compound (13) with a base is generally within a range of 0 to 80° C., and the reaction time is generally within a range of 0.5 to 24 hours.

The reaction mixture obtained by the reaction of the compound (13) with the base may be directly employed in the reaction with the compound (14). The reaction temperature in the reaction is generally within a range of 0 to 80° C., and the reaction time is generally within a range of 0.5 to 24 hours.

After the reaction is completed, the reaction mixture may be worked up, for example, by extraction with an organic solvent, drying and concentration, to isolate the compound (11). The isolated compound (11) may be further purified, for example, by chromatography, recrystallization or the like.

Reference Production Method 7:

The compound (13) can be also produced by reacting the compound (15) with a chlorination agent (16).

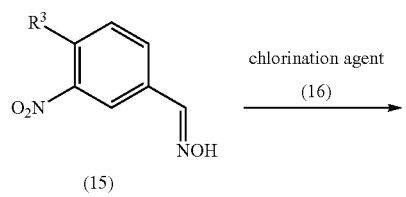

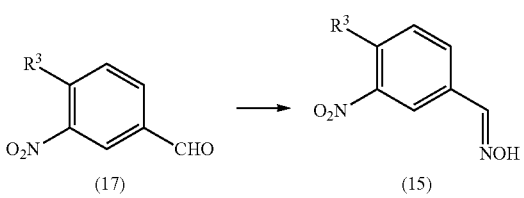

wherein R³ is as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; aromatic hydrocarbons such as toluene; esters such as ethyl acetate; acid amides such as N,N-dimethylformamide; alcohols such as ethanol and methanol; nitriles such as acetonitrile; sulfoxides such as dimethyl sulfoxide; water; and their mixtures.

Examples of the hydroxylamine to be used in the reaction include salts of hydroxylamine with a mineral acid such as hydroxylamine hydrochloride and hydroxylamine sulfate, which are capable of producing hydroxylamine in the reaction system. In this case, the reaction is performed in the presence of a base. Examples of the base include organic amines such as triethylamine; carbonates such as sodium carbonate; and alkali metal hydroxides such as sodium hydroxide.

In the above reaction, the amount of the hydroxylamine to be used is generally 1 to 10 mol relative to 1 mol of the compound (17). When the salt of hydroxylamine with a mineral acid is used, the amount of the base is generally 1 to 10 mol relative to 1 mol of the salt of hydroxylamine with a mineral acid.

In the above reaction, the reaction temperature is generally within a range of 0 to 80° C., and the reaction time is generally within a range of 0.5 to 24 hours.

After the reaction is completed, the reaction mixture may be worked up, for example, by extraction with an organic solvent, drying and concentration, to isolate the compound (15). The isolated compound (15) may be further purified, for example, by chromatography, recrystallization or the like.

Reference Production Method 9:

The compound (4) can be produced by reacting the compound (18) with a base, and then reacting the reaction mixture with the compound (14).

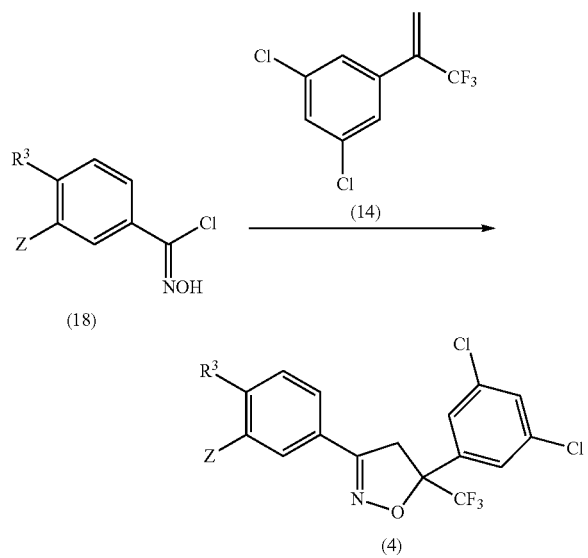

wherein $R^3$ and Z are as defined above.

The reaction is generally performed in a solvent.

Examples of the solvent to be used in the reaction include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; hydrocarbons such as toluene; esters such as ethyl acetate; sulfoxides such as dimethyl sulfoxide; and their mixtures.

Examples of the base to be used in the reaction include alkali metal hydrides such as sodium hydride; carbonates such as potassium carbonate; alkali metal alkoxides such as potassium tert-butoxide; and organic amines such as triethylamine and pyridine.

In the above reaction, the amount of the compound (14) to be used is generally 1 to 10 mol relative to 1 mol of the compound (18), and the amount of the base to be used is generally 1 to 10 mol relative to 1 mol of the compound (18).

In the reaction of the compound (18) with a base, the reaction temperature is generally within a range of 0 to 80° C., and the reaction time is generally within a range of 0.5 to 24 hours.

The reaction mixture obtained by the reaction of the compound (18) with a base can be directly used in the reaction with the compound (14). The reaction temperature in the reaction is generally within a range of 0 to 80° C., and the reaction time is generally 0.5 to 24 hours.

After the reaction is completed, the reaction mixture may be worked up, for example, by extraction with an organic solvent, drying and concentration, to isolate the compound (4). The isolated compound (4) may be further purified, for example, by chromatography, recrystallization or the like.

Examples of the animal ectoparasites to be controlled by the present hydrazide compound or the controlling agent of the present invention include as follows:

Fleas (Aphaniptera): *Pulex* spp. such as human flea (*Pulex irritans*); *Ctenocephalides* spp. such as cat flea (*Ctenocephalides felis*) and dog flea (*Ctenocephalides canis*); *Xenopsylla* spp. such as oriental rat flea (*Xenopsylla cheopis*); *Tunga* spp. such as chigoe (*Tunga penetrans*); *Echidnophaga* spp. such as chicken flea (*Echidnophaga gallinacea*); *Nosopsyllus* spp. such as European mouse flea (*Nosopsyllus fasciatus*); and the like.

Lice (Anoplura): *Pediculus* spp. such as head louse (*Pediculus humanus capitis*); *Phtirus* spp. such as crab louse (*Pthirus pubis*); *Haematopinus* spp. such as cattle louse (*Haematopinus eurysternus*) and hog louse (*Haematopinus suis*); *Damalinia* spp. such as sheep louse (*Dalmalinia ovis*) and *Damalinia bovis*; *Linognathus* spp. such as long nosed cattle louse (*Linognathus vituli*) and sheep face louse (*Linognathus ovillus*); *Solenopotes* spp. such as little blue cattle louse (*Solenopotes capillatus*); and the like.

Mallophages: *Menopon* spp. such as chicken louse (*Menopon gallinae*); *Trimenopon* spp.; *Trinoton* spp.; *Trichodectes* spp. such as dog biting louse (*Trichodectes canis*); *Felicola* spp. such as cat louse (*Felicola subrostratus*); *Bovicola* spp. such as cattle biting louse (*Bovicola bovis*); *Menacanthus* spp. such as chicken body louse (*Menacanthus stramineus*); *Werneckiella* spp.; and *Lepikentron* spp.; and the like.

Hemiptera: *Cimix* spp. such as bedbug (*Cimex lectularius*) and tropical bedbug (*Cimex hemipterus*); *Reduvius* spp. such as *Reduvius senilis*; *Arilus* spp. such as *Arilus critatus*; *Rhodnius* spp. such as *Rhodnius prolixus*; *Triatoma* spp. such as triatomine bug (*Triatoma rubrofasciata*); *Panstrongylus* ssp.; and the like.

Ticks (Acarina): *Amblyomma* spp. such as lone star tick (*Amblyomma americanum*) and *Ambryomma maculatum*; *Boophilus* spp. such as cattle tick (*Boophilus microplus*) and *Boophilus annulatus*; *Dermacentor* spp. such as American dog tick (*Dermacentor variabilis*), *Dermacentor taiwanicus* and *Dermacentor andersoni*; *Haemaphysalis* spp. such as bush tick (*Haemaphysalis longicornis*), *Haemaphysalis flava* and *Haemaphysalis campanulata*; *Ixodes* spp. such as *Ixodes ovatus*, taiga tick (*Ixodes persulcatus*), black legged tick (*Ixodes scapularis*), western black-legged tick (*Ixodes pacificus*) and *Ixodes holocyclus*; *Rhipicephalus* spp. such as brown dog tick (*Rhipicephalus sanguineus*) and *Rhipicephalus appendiculatus*; *Argas* spp. such as fowl tick (*Argas persicus*); *Ornithodorus* spp. such as *Ornithodorus hermsi* and *Ornithodorus turicata*; psoroptid mites such as sheep scab mite (*Psoroptes ovis*) and horse psoroptic mange mite (*Psoroptes equi*); *Knemidocoptes* spp. such as *Knemidocoptes mutans*; *Notoedres* spp. such as cat mange mite (*Notoedres cati*) and rat ear mange mite (*Notoedres muris*); *Sarcoptes* spp. such as itch mite (*Sarcoptes scabiei*); *Otodectes* spp. such as ear mite (*Octodectes cynotis*); *Listrophorus* such as rabbit fur mite (*Listrophorus gibbus*); *Chorioptes* spp.; *Hypodectes* spp.; *Pterolichus* spp.; *Cytodites* spp.; *Laminosioptes* spp.; *Dermanyssus* spp. such as parasitoid mite (*Dermanyssus gallinae*); *Ornithonyssus* spp. such as northern fowl mite (*Ornithonyssus sylviarum*) and house tick (*Orni-

*thonyssus bacoti*); *Varroa* spp. such as honey bee mite (*Varroa jacobsoni*); *Cheyletiella* spp. such as dog cheyletid mite (*Cheyletiella yasguri*) and cat mite (*Cheyletiella blakei*); *Ornithocheyletia* spp.; *Demodex* spp. such as dog follicle mite (*Demodex canis*) and cat follicle mite (*Demodex cati*); *Myobia* spp.; *Psorergates* spp.; akamushi), *Trombicula pallida* and *Trombicula scutellaris*.

Among these animal ectoparasites, fleas, lice and ticks are particularly exemplified.

The target animals to which the present hydrazide compound or the controlling agent of the present invention is applied are generally those to be hosts for the above animal ectoparasites, and include, for example, homeothermic animals and heterothermic animals that are reared as livestock or pets. Examples of the homeothermic animals include mammals such as cow, water buffalo, sheep, goat, pig, camel, deer, fallow deer, reindeer, horse, donkey, dog, cat, rabbit, ferret, mouse, rat, hamster, squirrel, and monkey; fur-bearing animals such as mink, chinchilla, and raccoon; and birds such as chicken, goose, turkey, duck, pigeon, parrot, and quail. Examples of the heterothermic animals include reptiles such as land turtle, sea turtle, *Trachemys scripta*, Reeve's pond turtle, lizard, iguana, chameleon, gecko, python, Colubridae, and cobra; and fish such as freshwater fish and salt-water fish, e.g., trout, carp, and eel. Preferred are homeothermic animals, and more preferred are mammals such as dog, cat, cow, horse, pig, sheep, and goat.

In the controlling agent of the present invention, the present hydrazide compound may be used alone, but is generally formulated with inert carriers such as solid carriers and liquid carriers, and optionally other formulation additives such as surfactants and the like. The controlling agent of the present invention is usually a formulation obtained by mixing inert carriers such as solid carriers and liquid carriers, and optionally adding thereto surfactants or other formulation additives. Examples of the formulation include liquid formulations such as emulsifiable concentrate, oil formulation, oily liquid formulation, aqueous liquid formulation, solution, shampoo, and suspension formulation; dusts; granules; paste formulation; cream; ointment; microencapsulated formulation; foaming formulation; aerosol formulation; carbon dioxide gas formulation; tablets; chewable tablets; bolus formulation; capsule formulation; animal feed premixes; syrup; sheet formulation, film-type formulation; resin formulation; injection formulation; implanted formulation; and suppository formulation. The suitable formulation is chosen when the present invention is employed.

The controlling agent of the present invention generally contains the present hydrazide compound in an amount of 0.001 to 99.9% by weight of the whole composition.

Examples of the solid carriers to be used in the formulation include natural or synthetic minerals such as clay, kaolin, talc, bentonite, sericite, quartz, sulfur, activated carbon, calcium carbonate, diatomaceous earth, pumice, calcite, sepiolite, white mica, silica, alumina, vermiculite, and perlite; small granules such as sawdust, corn spike, coconut shell, and tobacco stem; gelatin; vaseline; methylcellulose; lanolin; lard; liquid paraffin; and the like.

Examples of the liquid carriers include alcohols such as methanol, ethanol, isopropyl alcohol, butanol, and hexanol; polyhydric alcohols such as ethylene glycol, propylene glycol, dipropylene glycol, 1,3-butylene glycol, glycerine, and polyethylene glycol; ethers such as diethyl ether, ethyleneglycol dimethyl ether, diethyleneglycol monomethyl ether, diethyleneglycol monoethyl ether, propyleneglycol monomethyl ether, tetrahydrofuran, and dioxane; esters such as ethyl acetate, butyl acetate, and propylene carbonate; fatty acid esters such as diisopropyl adipate, diisobutyl adipate, and isopropyl myristate; ketones such as acetone, methyl ethyl ketone, methyl isobutyl ketone, and cyclohexanone; aromatic or aliphatic hydrocarbons such as xylene, toluene, alkylnaphthalene, phenylxylylethane, kerosene, gas oil, hexane, cyclohexane, and liquid paraffin; sulfoxides such as dimethyl sulfoxide; acid amides such as N,N-dimethylformamide and N,N-dimethylacetoamide; N-methyl-2-pyrrolidone, γ-butyrolactone; vegetable oils such as soybean oil, cottonseed oil, castor oil, and palm oil; plant essential oil such as orange oil, hyssop oil, and lemon oil; silicone oils such as dimethyl silicone oil, high-molecular-weight dimethyl silicone oil, cyclic silicone oil, polyether modified silicone oil, amino modified silicone oil, and methylphenyl silicone oil; water and the like.

Examples of the surfactants include nonionic surfactants, ampholytic surfactants, anionic surfactants, and cationic surfactants, specifically as follows:

Nonionic surfactants: sorbitan fatty acid esters such as sorbitan stearate, and sorbitan oleate; glycerine fatty acid esters such as glyceryl stearate, glyceryl isostearate, glyceryl oleate, polyglyceryl stearate, polyglyceryl isostearate, and polyglyceryl oleate; polyoxyethylene alkyl ethers such as polyoxyethylene lauryl ether, polyoxyethylene cetyl ether, polyoxyethylene stearyl ether, polyoxyethylene oleyl ether, and polyoxyethylene styryl phenyl ether; polyoxyethylene sorbitan fatty acid esters such as polyoxyethylene sorbitan coconut oil fatty acid esters, polyoxyethylene sorbitan oleate, and polyoxyethylene sorbitan stearate; polyoxyethylene sorbit fatty acid esters such as polyoxyethylene sorbit tetraoleate; polyoxyethylene-cured castor oil, alkylphenol polyglycol ether; and the like.

Ampholytic surfactants: betaines such as laurylbetaine and stearylbetaine; imidazoline derivatives such as disodium N-lauryl-p-iminodipropionate; lecithins; and the like.

Anionic surfactants: alkyl sulfates such as sodium lauryl sulfate and triethanolamine lauryl sulfate; polyoxyethylene alkyl ether sulfates such as sodium lauryl polyoxyethylene ether sulfate and triethanolamine polyoxyethylene lauryl ether sulfate; alkylbenzene sulfonate such as sodium dodecylbenzene sulfonate; polyoxyethylene alkyl ether phosphates such as sodium dipolyoxyethylene lauryl ether phosphate and sodium dipolyoxyethylene oleyl ether phosphate.

Cationic surfactants: alkyl ammonium salts such as cetyltrimethyl ammonium chloride, and distearyl dimethyl ammonium chloride.

Other formulation additives include, for example, dispersing agents, antioxidants, coloring agents, light stabilizers, adhesives, and the like.

Examples of the dispersing agents include lignin sulfonate and methylcellulose.

Examples of the antioxidants include BHT and BHA.

Examples of the coloring agents include food tar colors such as Red No. 2 (Amaranth), Red No. 3 (Erythrosine), Yellow No. 4 (Tartrazine), Green No. 3 (Fast Green FCF), and Blue No. 1 (Brilliant Blue FCF); iron oxide, titanium oxide, Prussian blue, alizarin dyes, azo dyes, and phthalocyanine dyes.

Examples of the light stabilizers include benzophenone compounds, benzoate compounds, and benzotriazol compounds.

Examples of the adhesives include bentonite, colloidal silicic acid, cellulose derivatives, starch derivatives, polyacrylates, natural polymers, alginic acid salts, and gelatin.

Examples of binders in the tablets and chewable tablets include methylcellulose, carboxymethylcellulose, ethylhydroxyethylcellulose; protein derivatives such as zein and gelatin; synthetic polymers such as polyvinyl alcohol and polyvinyl pyrrolidone; starch, and celluloses.

In addition, the tablets and chewable tablets may contain fillers such as starch, microcrystalline cellulose, sugar, and lactose; lubricants such as magnesium stearate and talc; disintegrants such as starch, cellulose, and carbonates.

The tablets can be produced by, for example, mixing the present hydrazide compound, binders and the like, and compressing the resulting mixture to a suitable size. Tablets may be coated, if desired. Examples of the coating agent to be used for coating tablets include those containing acetic acid-phthalic acid cellulose, diethyl phthalate, ethanol, and dichloromethane; those containing hydroxypropylcellulose, polyethylene glycol, water, and titanium dioxide; enteric film coating agents such as polyvinyl acetal diethylaminoacetate; and other film forming materials such as food coloring agents, and hydroxypropyl methylcellulose containing aqueous or non-aqueous solvents. The film coating agents may contain plasticizers or coloring agents.

Examples of propellants for the foaming formulation, aerosol formulation, or carbon dioxide gas formulation include propane gases, butane gas, Freon gases, liquefied petroleum gases, dimethyl ether, and carbon dioxide gases.

Examples of bases for the resin formulation include vinyl chloride polymers, ethylene copolymers, polyurethanes, polyethylenes, polypropylenes, and polyethylene terephthalate. The bases optionally contain phthalic acid esters such as dimethyl phthalate and dioctyl phthalate; and plasticizers such as adipic acid esters and stearic acid. The resin formulation can be formed into, for example, animal collars, animal ear tags and the like, by kneading the present hydrazide compound into the base with a common kneading machine, and then forming the mixture by injection molding, extrusion molding, press molding, or the like. If necessary, the molded products may be further processed by shape forming, cutting, or the like to obtain animal ear tags and the like.

Examples of capsules for the capsule formulation include gelatin capsules and hydroxypropyl methylcellulose capsules.

Examples of bases for the suppository include cacao butter, laurin butter, polyethylene glycol, glycerogelatin, sodium stearate, witepsol, and their mixtures.

The controlling agent of the present invention may be used in mixture or combination with commonly known other insecticides, agents for killing animal parasitic mites, or agents for killing endoparasites. In addition, the controlling agent of the present invention may also be used in mixture or combination with repellents.

The animal ectoparasite-controlling method according to the present invention (hereinafter referred to as "the controlling method of the present invention") comprises applying an effective amount of the present hydrazide compound to an animal.

According to the controlling method of the present invention, the present hydrazide compound can therapeutically, suppressively, prophylactically or protectively act on animal ectoparasites.

By the controlling method of the present invention, animal ectoparasites may be suppressed systemically or nonsystemically. The controlling method of the present invention can be applied to animal ectoparasites at all or any developmental stages.

In the controlling method of the present invention, the present hydrazide compound can be administered orally or parenterally to a host animal. Examples of the oral administration method include the administration of the present hydrazide compound in the form of an oral formulation to an animal. Examples of the parenteral administration method include the application of the present hydrazide compound in the form of an external preparation for skin, injection formulation, suppository, implanted formulation, or resin formulation in suitable shape such as collar or ear tag to an animal.

(1) Oral Administration:

In the controlling method of the present invention, the present hydrazide compound may be orally administered to an animal in the form of, for example, liquid formulations such as emulsifiable concentrate, oil solutions, oily liquid formulation, aqueous liquid formulation, solution, suspension formulation; gel; dusts; granules; paste formulation; tablets; chewable tablets; bolus formulation; capsule formulation; animal feed premix; or syrup.

(2) Parenteral Administration:

(a) External Application to Skin:

In the controlling method of the present invention, the present hydrazide compound may be externally applied to the skin of an animal, for example, in the form of liquid formulations such as emulsifiable concentrate, oil solution, oily liquid formulation, aqueous liquid formulation, solution, shampoo, or suspension formulation; dusts; cream; ointment; aerosol formulation, or sheet formulation, by spot-on application, pour-on application, immersing, spraying, coating, bathing, washing, rubbing, dispersing, or the like. Preferred application methods are spot-on application and pour-on application.

The spot-on application generally means the dropping or coating application of a liquid formulation onto the skin from head to tail of a host animal.

The pour-on application generally means the pouring application of a liquid formulation along the back line of a host animal.

In this case, the present hydrazide compound can be formulated into a liquid formulation by using the above liquid carriers.

(b) Injection Application:

In the controlling method of the present invention, the present hydrazide compound in the form of injection formulation may be applied to an animal by intraruminal injection, intramuscular injection, intravenous injection, or subcutaneous injection.

(c) Other Applications:

In the controlling method of the present invention, the present hydrazide compound may be applied to an animal in the form of a suppository, implanted formulation, or resin formulation in suitable shape such as collar or ear tag.

The amount of the present hydrazide compound to be applied to an animal may vary depending on the type of the target animal or animal ectoparasite to be controlled, but is generally 1 to 5000 mg/kg-living body weight of the animal. When the present hydrazide compound is orally administered or applied by injection, the amount is preferably 1 to 100 mg/kg. In the oral administration, the amount is more preferably 1 to 50 mg/kg, and most preferably 5 to 50 mg/kg. When the present hydrazide compound is externally applied to the skin, the amount is preferably 1 to 1000 mg/kg, more preferably 1 mg/kg to 100 mg/kg, and most preferably 5 to 50 mg/kg.

EXAMPLES

Hereinafter, the present invention will be explained in detail with reference to Production Examples of the present hydrazide compounds, Reference Production Examples of the intermediates for the production of the present hydrazide compounds, Formulation Examples of the controlling agents of the present invention and Test Example, but the present invention should not be interpreted to be limited to these examples.

In the present specification, Me represents a methyl group.

Production Example 1

To crude tert-butyl N'-methoxyacetyl-N-{2-chloro-5-[5-(3,5-dichlorophenyl)-5-trifluoromethyl-4,5-dihydroisoxazol-3-yl]phenyl}carbazate (309 mg) obtained by Reference Production Example 11 was added trifluoroacetic acid (2 mL) at room temperature, and the mixture was stirred at the same temperature for 2 hours. The reaction mixture was concentrated under reduced pressure. To the residue was added ethyl acetate, and the organic layer was washed with an aqueous saturated sodium hydrogen carbonate solution. The organic layer was dried over anhydrous sodium sulfate and concentrated under reduced pressure. The resulting residue was subjected to silica gel column chromatography to obtain N'-{2-chloro-5-[5-(3,5-dichlorophenyl)-5-trifluoromethyl-4,5-dihydroisoxazol-3-yl]phenyl}methoxyacetohydrazide (276 mg; hereinafter referred to as "the present hydrazide compound (1)").

The present hydrazide compound (1):

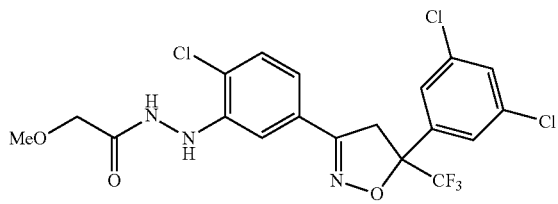 [SMILES: COCC(=O)NNc1cc(C2=NOC(c3cc(Cl)cc(Cl)c3)(C(F)(F)F)C2)ccc1Cl]

Melting point: 178° C.

Hereinafter, Reference Production Examples of the intermediates for the production of the present hydrazide compounds will be described:

Reference Production Example 1

In dimethylformamide (30 mL), 2-chloro-5-hydroxyiminomethylnitrobenzene (2.92 g) and N-chlorosuccinimide (1.94 g) were dissolved, and the mixture was stirred at 60° C. for 1 hour. The mixture was cooled to room temperature, and thereto was added 2-(3,5-dichlorophenyl)-3,3,3-trifluoro-1-propene (3.50 g), followed by triethylamine (1.46 g), and then the mixture was stirred for 6 hours. To the reaction mixture was added water and the mixture was extracted with ethyl acetate. The organic layer was dried over anhydrous sodium sulfate and concentrated under reduced pressure. The resulting residue was subjected to silica gel column chromatography to obtain 5-[5-(3,5-dichlorophenyl)-5-trifluoromethyl-4,5-dihydroisoxazol-3-yl]-2-chloronitrobenzene (4.42 g).

5-[5-(3,5-dichlorophenyl)-5-trifluoromethyl-4,5-dihydroisoxazol-3-yl]-2-chloronitrobenzene

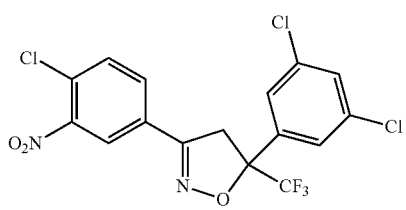 [SMILES: O=[N+]([O-])c1cc(C2=NOC(c3cc(Cl)cc(Cl)c3)(C(F)(F)F)C2)ccc1Cl]

$^1$H-NMR (CDCl$_3$) d: 8.09 (1H, d, J=2.1 Hz), 7.89 (1H, dd, J=8.5, 2.1 Hz), 7.65 (1H, d, J=8.5 Hz), 7.50 (2H, d, J=1.6 Hz), 7.45 (1H, t, J=1.6 Hz), 4.09 (1H, d, J=17.3 Hz), 3.71 (1H, d, J=17.3 Hz).

Reference Production Example 2

An iron powder (3.46 g) was added to a mixture of acetic acid (0.38 g), water (15 ml) and ethanol (30 mL) at room temperature, and thereto was added 5-[5-(3,5-dichlorophenyl)-5-trifluoromethyl-4,5-dihydroisoxazol-3-yl]-2-chloronitrobenzene (2.73 g) obtained by Reference Production Example 1 at 75° C. After stirring at 75° C. for 50 minutes, the reaction mixture was filtrated and then the filtrate was concentrated under reduced pressure. The resulting residue was subjected to silica gel column chromatography to obtain 5-[5-(3,5-dichlorophenyl)-5-trifluoromethyl-4,5-dihydroisoxazol-3-yl]-2-chloroaniline (1.65 g).

5-[5-(3,5-dichlorophenyl)-5-trifluoromethyl-4,5-dihydroisoxazol-3-yl]-2-chloroaniline

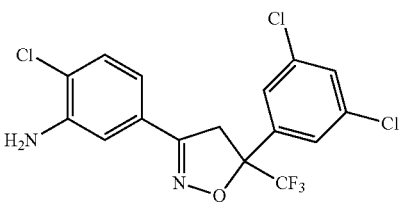

$^1$H-NMR (CDCl$_3$) d: 7.49 (2H, d, J=1.7 Hz), 7.42 (1H, t, J=1.7 Hz), 7.29 (1H, d, J=8.4 Hz), 7.13 (1H, d, J=2.0 Hz), 6.89 (1H, dd, J=8.4, 2.0 Hz), 4.18 (2H, br s), 4.03 (1H, d, J=17.1 Hz), 3.64 (1H, d, J=16.4 Hz).

Reference Production Example 3

In 1,4-dioxane (2 ml), 5-[5-(3,5-dichlorophenyl)-5-trifluoromethyl-4,5-dihydroisoxazol-3-yl]-2-chloroaniline (500 mg) obtained by Reference Production Example 2 was dissolved, and thereto was added a concentrated hydrochloric acid (6 mL) at room temperature. After stirring at the same temperature for 20 minutes, this solution was cooled to 0° C., and thereto was added dropwise a solution of sodium nitrite (93 mg) in water (3 mL), and then the mixture was stirred at the same temperature for 15 minutes. To this reaction mixture was added dropwise a solution of tin(II) chloride (507 mg) in a concentrated hydrochloric acid (4 mL). Then, the reaction mixture was neutralized with 2N sodium hydroxide, and the aqueous layer was extracted with t-butyl methyl ether. The organic layer was dried over anhydrous sodium sulfate and concentrated under reduced pressure to obtain crude 5-[5-(3,5-dichlorophenyl)-5-trifluoromethyl-4,5-dihydroisoxazol-3-yl]-2-chlorophenylhydrazine (510 mg).

5-[5-(3,5-dichlorophenyl)-5-trifluoromethyl-4,5-dihydroisoxazol-3-yl]-2-chlorophenylhydrazine

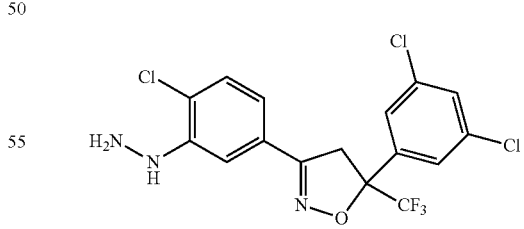

Reference Production Example 4

Triphosgene (6.3 g) was dissolved in toluene (50 mL), and thereto was added dropwise a solution of 5-[5-(3,5-dichlorophenyl)-5-trifluoromethyl-4,5-dihydroisoxazol-3-yl]-2-chloroaniline (8.7 g) obtained by Reference Production Example 2 in toluene (50 mL) and tetrahydrofuran (10 mL) at room temperature. To the reaction solution was added toluene (50 mL), and the mixture was stirred at 80° C. for 1 hour. After cooling to room temperature, the reaction mixture was concentrated under reduced pressure, and thereto was added tert-butanol (100 mL). To this solution was added dropwise triethylamine (14.6 g) at room temperature, and the mixture was stirred at the same temperature for 16 hours. To the reaction mixture was added an aqueous saturated sodium hydrogen carbonate solution, and the mixture was extracted with chloroform. The organic layer was dried over anhydrous sodium sulfate and concentrated under reduced pressure. The resulting residue was subjected to silica gel column chromatography to obtain tert-butyl {2-chloro-5-[5-(3,5-dichlorophenyl)-5-trifluoromethyl-4,5-dihydroisoxazol-3-yl]phenyl}carbamate (9.81 g).

Tert-butyl {2-chloro-5-[5-(3,5-dichlorophenyl)-5-trifluoromethyl-4,5-dihydroisoxazol-3-yl]phenyl}carbamate

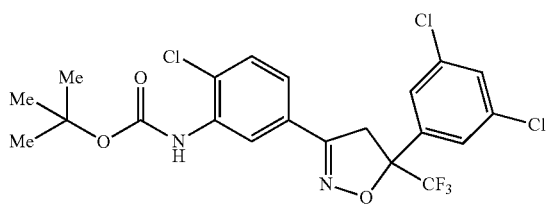 [SMILES: CC(C)(C)OC(=O)Nc1cc(C2=NOC(c3cc(Cl)cc(Cl)c3)(C(F)(F)F)C2)ccc1Cl]

$^1$H-NMR (CDCl$_3$) d: 8.39 (1H, d, J=2.1 Hz), 7.52 (2H, d, J=1.8 Hz), 7.47 (1H, dd, J=8.5, 2.1 Hz), 7.42 (1H, t, J=1.8 Hz), 7.39 (1H, d, J=8.5 Hz), 7.09 (1H, br s), 4.11 (1H, d, J=17.3 Hz), 3.70 (1H, d, J=17.3 Hz), 1.55 (9H, s).

Reference Production Example 5

Sodium hydride (60% oily; 760 mg) was suspended in tetrahydrofuran (200 mL), and thereto was added dropwise a solution of tert-butyl {2-chloro-5-[5-(3,5-dichlorophenyl)-5-trifluoromethyl-4,5-dihydroisoxazol-3-yl]phenyl}carbamate (8.80 g) obtained by Reference Production Example 4 in tetrahydrofuran (50 mL) at room temperature, and then the mixture was stirred at the same temperature for 20 minutes. To the mixture was added O-(diphenylphosphoryl)-hydroxylamine (6.0 g) at room temperature, and the mixture was stirred at the same temperature for 15 hours. To the mixture were added water and ethyl acetate, and the aqueous layer was extracted with ethyl acetate. The organic layer was dried over anhydrous sodium sulfate and concentrated under reduced pressure. The resulting residue was subjected to silica gel column chromatography to obtain tert-butyl N-{2-chloro-5-[5-(3,5-dichlorophenyl)-5-trifluoromethyl-4,5-dihydroisoxazol-3-yl]phenyl}carbazate (6.58 g).

Tert-butyl N-{2-chloro-5-[5-(3,5-dichlorophenyl)-5-trifluoromethyl-4,5-dihydroisoxazol-3-yl]phenyl}carbazate

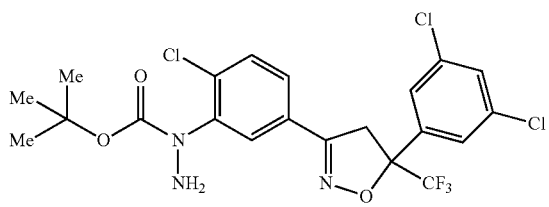 [SMILES: CC(C)(C)OC(=O)N(N)c1cc(C2=NOC(c3cc(Cl)cc(Cl)c3)(C(F)(F)F)C2)ccc1Cl]

$^1$H-NMR (CDCl$_3$) d: 7.55-7.44 (6H, m), 4.07 (1H, d, J=17.1 Hz), 3.68 (1H, d, J=17.1 Hz), 1.41 (9H, br s).

Reference Production Example 6

In tetrahydrofuran (20 mL), 5-[5-(3,5-dichlorophenyl)-5-trifluoromethyl-4,5-dihydroisoxazol-3-yl]-2-chloroaniline (3.04 g) obtained by Reference Production Example 2 and triethylamine (772 mg) were dissolved, and thereto was added dropwise trifluoroacetic acid anhydride (1.47 g) at 0° C. After stirring at the same temperature for 30 minutes, the reaction mixture was diluted with tert-butyl methyl ether. To the reaction mixture was added ethyl acetate, and the organic layer was washed with 2N hydrochloric acid, followed by an aqueous saturated sodium hydrogen carbonate solution. The organic layer was dried over anhydrous sodium sulfate and concentrated under reduced pressure to obtain N-{2-chloro-5-[5-(3,5-dichlorophenyl)-5-trifluoromethyl-4,5-dihydroisoxazol-3-yl]phenyl}2,2,2-trifluoroacetamide (3.63 g).

N-{2-chloro-5-[5-(3,5-dichlorophenyl)-5-trifluoromethyl-4,5-dihydroisoxazol-3-yl]phenyl}2,2,2-trifluoroacetamide

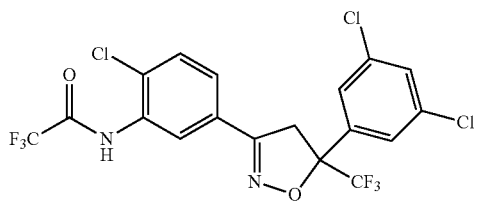 [SMILES: O=C(Nc1cc(C2=NOC(c3cc(Cl)cc(Cl)c3)(C(F)(F)F)C2)ccc1Cl)C(F)(F)F]

$^1$H-NMR (CDCl$_3$) d: 8.53 (1H, d, J=2.2 Hz), 8.48 (1H, br s), 7.67 (1H, dd, J=8.5, 2.0 Hz), 7.52 (1H, d, J=8.5 Hz), 7.50 (2H, s), 7.43-7.42 (1H, m), 4.09 (1H, d, J=17.3 Hz), 3.71 (1H, d, J=17.3 Hz).

Reference Production Example 7

Sodium hydride (600 oily) was suspended in N,N-dimethylformamide (15 mL), and thereto was added dropwise a solution of {N-{2-chloro-5-[5-(3,5-dichlorophenyl)-5-trifluoromethyl-4,5-dihydroisoxazol-3-yl]phenyl}-2,2,2-trifluoroacetamide (3.6 g) obtained by Reference Production Example 6 in N,N-dimethylformamide (15 mL) at room temperature, and then the mixture was stirred at the same temperature for 20 minutes. To the mixture was added methyl iodide (1.52 g), and the mixture was further stirred for 1 hour. To the reaction mixture was added 2N hydrochloric acid, and the mixture was extracted with tert-butyl methyl ether. The organic layer was dried over anhydrous sodium sulfate and concentrated under reduced pressure to obtain N-methyl-N-{2-chloro-5-[5-(3,5-dichlorophenyl)-5-trifluoromethyl-4,5-dihydroisoxazol-3-yl]phenyl}-2,2,2-trifluoroacetamide (3.73 g).

N-methyl-N-{2-chloro-5-[5-(3,5-dichlorophenyl)-5-trifluoromethyl-4,5-dihydroisoxazol-3-yl]phenyl}-2,2,2-trifluoroacetamide

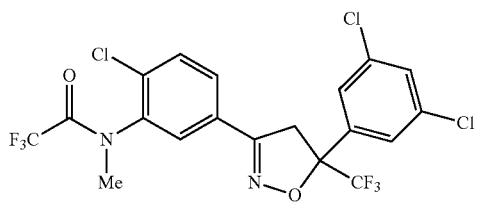 [SMILES: CN(C(=O)C(F)(F)F)c1cc(C2=NOC(c3cc(Cl)cc(Cl)c3)(C(F)(F)F)C2)ccc1Cl]

$^1$H-NMR (CDCl$_3$) d: 7.70-7.40 (6H, m), 4.06 (1H, dd, J=17.2, 13.0 Hz), 3.73-3.64 (1H, m), 3.33-3.32 (3H, m).

Reference Production Example 8

N-methyl-N-{2-chloro-5-[5-(3,5-dichlorophenyl)-5-trifluoromethyl-4,5-dihydroisoxazol-3-yl]phenyl}2,2,2-trifluoroacetamide (3.6 g) obtained by Reference Production Example 7 was dissolved in methanol (20 mL), and thereto was added potassium carbonate (1.97 g) at room temperature, and the mixture was stirred at the same temperature for 3 hours. The precipitate was filtrated off, and to the filtrate was added water, and then the mixture was extracted with t-butyl methyl ether. The organic layer was dried over anhydrous sodium sulfate and concentrated under reduced pressure to obtain N-methyl-2-chloro-5-[5-(3,5-dichlorophenyl)-5-trifluoromethyl-4,5-dihydroisoxazol-3-yl]aniline (2.20 g).

N-methyl-2-chloro-5-[5-(3,5-dichlorophenyl)-5-trifluoromethyl-4,5-dihydroisoxazol-3-yl]aniline

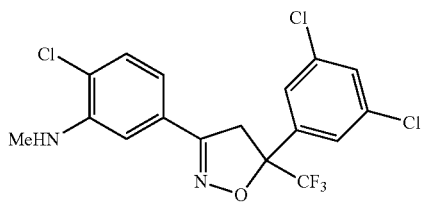 [SMILES: CNc1cc(C2=NOC(c3cc(Cl)cc(Cl)c3)(C(F)(F)F)C2)ccc1Cl]

$^1$H-NMR (CDCl$_3$) d: 7.51 (2H, d, J=1.8 Hz), 7.42 (1H, t, J=1.8 Hz), 7.28 (1H, d, J=8.0 Hz), 6.99 (1H, d, J=2.0 Hz), 6.78 (1H, dd, J=8.0, 2.0 Hz), 4.48 (1H, d, J=5.1 Hz), 4.07 (1H, d, J=17.2 Hz), 3.67 (1H, d, J=17.2 Hz), 2.94 (3H, d, J=5.1 Hz).

Reference Production Example 9

N-methyl-2-chloro-5-[5-(3,5-dichlorophenyl)-5-trifluoromethyl-4,5-dihydroisoxazol-3-yl]aniline (2.55 g) obtained by Reference Production Example 8 was dissolved in tetrahydrofuran (4 mL), and thereto was added a concentrated hydrochloric acid (4.5 mL), followed by water (5.0 mL). After stirring at room temperature for 10 minutes, this mixture was cooled to 0° C., and thereto was added dropwise a solution of sodium nitrite (539 mg) in water (5 mL). After stirring at the same temperature for 1 hour, the mixture was neutralized with an aqueous saturated sodium hydrogen carbonate solution, and then extracted with ethyl acetate. The organic layer was dried over anhydrous sodium sulfate and concentrated under reduced pressure to obtain N-methyl-N-nitroso-2-chloro-5-[5-(3,5-dichlorophenyl)-5-trifluoromethyl-4,5-dihydroisoxazol-3-yl]aniline (2.69 g).

N-methyl-N-nitroso-2-chloro-5-[5-(3,5-dichlorophenyl)-5-trifluoromethyl-4,5-dihydroisoxazol-3-yl]aniline

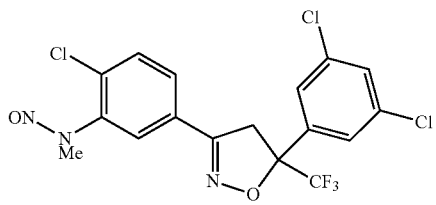

$^1$H-NMR (CDCl$_3$) d: 7.84-7.31 (6H, m), 4.09 (1H, d, J=17.3 Hz), 3.71 (1H, d, J=17.3 Hz), 3.41 (3H, s).

Reference Production Example 10

N-methyl-N-nitroso-2-chloro-5-[5-(3,5-dichlorophenyl)-5-trifluoromethyl-4,5-dihydroisoxazol-3-yl]aniline (2.61 g) obtained by Reference Production Example 9 was dissolved in tetrahydrofuran (4 mL), and thereto was added ethanol (8 mL), water (8 mL), and acetic acid (8 mL) in sequence at room temperature. To this mixture was added zinc (695 mg) at room temperature. After stirring at room temperature for 3 hours, this mixture was filtrated. Then, anhydrous sodium hydrogen carbonate was added to the filtrate, and the mixture was extracted with ethyl acetate. The organic layer was dried over anhydrous sodium sulfate and concentrated under reduced pressure. The resulting residue was subjected to silica gel column chromatography to obtain N-methyl-N-{2-chloro-5-[5-(3,5-dichlorophenyl)-5-trifluoromethyl-4,5-dihydroisoxazol-3-yl]phenyl}hydrazine (764 mg).

N-methyl-N-{2-chloro-5-[5-(3,5-dichlorophenyl)-5-trifluoromethyl-4,5-dihydroisoxazol-3-yl]phenyl}hydrazine

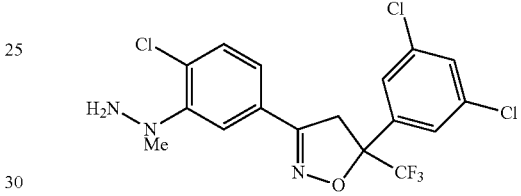

$^1$H-NMR (CDCl$_3$) d: 7.68-7.67 (1H, m), 7.51 (2H, s), 7.42-7.40 (2H, m), 7.23-7.20 (1H, m), 4.08 (1H, d, J=17.2 Hz), 3.85 (2H, br s), 3.69 (1H, d, J=17.2 Hz), 3.06 (3H, s).

Reference Production Example 11

Tert-butyl N-{2-chloro-5-[5-(3,5-dichlorophenyl)-5-trifluoromethyl-4,5-dihydroisoxazol-3-yl]phenyl}carbazate (367 mg) obtained by Reference Production Example 5 and triethylamine (84 mg) were dissolved in tetrahydrofuran (2 mL), and thereto was added dropwise methoxyacetyl chloride (91 mg) at room temperature for 1 hour. To the reaction mixture was added ethyl acetate, and the organic layer was washed with water. The organic layer was dried over anhydrous sodium sulfate and concentrated under reduced pressure to obtain crude tert-butyl N'-methoxyacetyl-N-{2-chloro-5-[5-(3,5-dichlorophenyl)-5-trifluoromethyl-4,5-dihydroisoxazol-3-yl]phenyl}carbazate (377 mg).

Tert-butyl N'-methoxyacetyl-N-{2-chloro-5-[5-(3,5-dichlorophenyl)-5-trifluoromethyl-4,5-dihydroisoxazol-3-yl]phenyl}carbazate

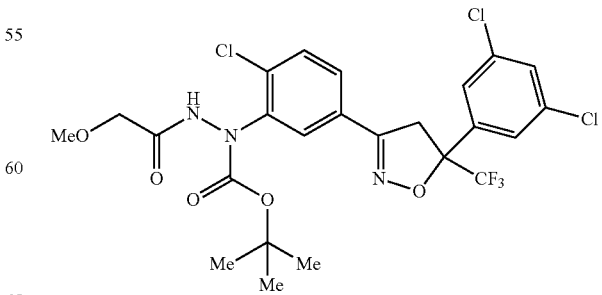

Hereinafter, Formulation Examples of the controlling agent of the present invention will be described:

Formulation Example 1

Tablets

The present hydrazide compound (1) (100 mg), lactose (68.75 mg), a corn starch (237.5 mg), a microcrystalline cellulose (43.75 mg), a polyvinyl pyrrolidone (18.75 mg), a sodium carboxymethyl starch (28.75 mg), and magnesium stearate (2.5 mg) are mixed together, and the resulting mixture is compressed into tablets of suitable size.

Formulation Example 2

Tablets

The present hydrazide compound (1) (25 mg), D-mannitol (73 g), a corn starch (30 mg), a low-substituted hydroxypropyl cellulose (7 mg), an aqueous 5% hydroxypropyl cellulose solution (appropriate amount), and magnesium stearate (appropriate amount) are mixed together, and the resulting mixture is compressed into tablets of suitable size.

Formulation Example 3

Tablets

The present hydrazide compound (1) (400 mg), a corn starch (50 mg), a croscarmellose sodium (25 mg), lactose (120 mg), and magnesium stearate (5 mg) are mixed together, and the resulting mixture is compressed into tablets of suitable size.

Formulation Example 4

Tablets

The present hydrazide compound (1) (60 mg), a microcrystalline cellulose (45 mg), a polyvinyl pyrrolidone (4 mg), a carboxymethyl starch sodium (4.5 mg), magnesium stearate (0.5 mg), and a talc (1 mg) are mixed together, and the resulting mixture is compressed into tablets of suitable size.

Formulation Example 5

Tablets

The present hydrazide compound (1) (10 mg), a starch (15 mg), lactose (127 mg), a carboxymethylcellulose calcium (15 mg), magnesium stearate (1 mg), and a talc (2 mg) are mixed together, and the resulting mixture is compressed into tablets of suitable size.

Formulation Example 6

Tablets

The present hydrazide compound (1) (100 mg), a dextrin (600 mg), a potato starch (200 mg), an animal feed powder (60 mg), a sesame oil (20 mg), and water (20 mg) are mixed together, and the resulting mixture is compressed into tablets of suitable size.

Formulation Example 7

Tablets

The present hydrazide compound (1) (100 mg), lactose (33 mg), a corn starch (16 mg), a carboxymethylcellulose calcium (12 mg), a methylcellulose (6 mg), and magnesium stearate (2 mg) are mixed together, and the resulting mixture is compressed into tablets of suitable size.

Formulation Example 8

Tablets

The present hydrazide compound (1) (10 mg), Fine Particles for Direct Compressing No. 209 (manufactured by Fuji Chemical Industry Co., Ltd.) (46.6 mg), magnesium aluminometasilicate (20%), a corn starch (30%), lactose (50%), a crystal cellulose (24 mg), a carboxymethylcellulose calcium (4 mg), and magnesium stearate (0.4 mg) are mixed together, and the resulting mixture is compressed into tablets of suitable size.

Formulation Example 9

Tablets

The present hydrazide compound (1) (250 mg), magnesium stearate (4.5 mg), a corn starch (22.5 mg), a sodium starch glycolate (9 mg), lauryl sodium sulfate (4.5 mg), and a microcrystalline cellulose (159.5 mg) are mixed together, and the mixture is compressed into tablets of suitable size.

Formulation Example 10

Tablets

The present hydrazide compound (1) (250 mg), lactose (101.5 mg), a wheat flour starch (6.5 mg), polyethylene glycol 6000 (5 mg), a talc (5 mg), magnesium stearate (2 mg), and deionized water (appropriate amount) are mixed together, and the mixture is compressed into tablets of suitable size.

Formulation Example 11

Tablets

The present hydrazide compound (1) (200 mg), lactose (200 mg), a potato starch (266.5 mg), stearic acid (10 mg), a talc (217 mg), magnesium stearate (2.5 mg), a colloidal silica (32 mg), and ethanol (appropriate amount) are mixed together, and the mixture is compressed into tablets of suitable size.

Formulation Example 12

Tablets

The present hydrazide compound (1) (50 mg), magnesium stearate (7.5 mg), and a microcrystalline cellulose (17.5 mg) are mixed together, and the mixture is compressed into tablets of suitable size.

Formulation Example 13

Tablets

Each of the tablets obtained by Formulation Examples 1 to 12 is coated with a coating agent containing a mixture of 20% acetic acid-phthalic acid cellulose, 3% diethyl phthalate, ethanol, and dichloromethane in equal amounts to obtain the coated tablets.

Formulation Example 14

Tablets

Each of the tablets obtained by Formulation Examples 1 to 12 is coated with a coating agent obtained by dissolving hydroxypropyl cellulose 2910 (10.8 g) and polyethylene glycol 6000 (2.1 g) in a purified water (172.5 g) and dispersing thereinto titanium dioxide (2.1 g) to obtain the coated tablets.

Formulation Example 15

Capsule Formulation

The present hydrazide compound (1) (25 mg), lactose (60 mg), a corn starch (25 mg), a carmellose calcium (6 mg), and 5% hydroxypropyl methylcellulose (appropriate amount) are mixed together, and the resulting mixture is filled into hard-shell gelatin capsules or hydroxypropyl methylcellulose capsules to obtain a capsule formulation.

Formulation Example 16

Capsule Formulation

The present hydrazide compound (1) (200 mg), lactose (148 mg), and magnesium stearate (2 mg) are mixed together, and the resulting mixture is filled into hard-shell gelatin capsules or hydroxypropyl methylcellulose capsules to obtain a capsule formulation.

Formulation Example 17

Capsule Formulation

The present hydrazide compound (1) (250 mg), a dry starch (200 mg), and magnesium stearate (10 mg) are mixed together, and the resulting mixture is filled into hard-shell gelatin capsules or hydroxypropyl methylcellulose capsules to obtain a capsule formulation.

Formulation Example 18

Capsule Formulation

The present hydrazide compound (1) (250 mg), a microcrystalline cellulose (400 mg), a fumed silicon dioxide (10 mg), and stearic acid (5 mg) are mixed together, and the resulting mixture is filled into hard-shell gelatin capsules or hydroxypropyl methylcellulose capsules to obtain a capsule formulation.

Formulation Example 19

Capsule Formulation

The present hydrazide compound (1) (20 mg), lactose (251.8 mg), gelatin (2 mg), a corn starch (10 mg), talc (15 mg), and water (appropriate amount) are mixed together, and the resulting mixture is filled into hard-shell gelatin capsules or hydroxypropyl methylcellulose capsules to obtain a capsule formulation.

Formulation Example 20

Oral Suspension Formulation

The present hydrazide compound (1) (1000 mg), fumaric acid (500 mg), sodium chloride (2000 mg), methylparaben (150 mg), propylparaben (50 mg), a granulated sugar (25000 mg), sorbitol (70% solution; 13000 mg), VeegumK (Vanderbilt Co.; 100 mg), a fragrance (35 mg), a colorant (500 mg) and distilled water (added to the final volume of 100 mL) are mixed together to obtain an oral suspension formulation.

Formulation Example 21

Oral Suspension Formulation

The present hydrazide compound (1) (50 mg), a carboxymethylcellulose sodium (50 mg), a syrup (1.25 ml), a benzoic acid solution (0.1 ml), a fragrance (appropriate amount), a colorant (appropriate amount) and distilled water (added to the final volume of 5 mL) are mixed together to obtain an oral suspension formulation.

Formulation Example 22

Oral liquid formulation

The present hydrazide compound (1) (5% by weight) is dissolved in polysorbate 85 (5% by weight), benzyl alcohol (3% by weight), and propylene glycol (30% by weight). This solution is adjusted to pH 6.0 to 6.5 by adding a phosphate buffer, and thereto is added water to be a desired final volume to obtain an oral liquid formulation.

Formulation Example 23

Oral liquid formulation

The present hydrazide compound (1) (10% by weight) is homogeneously dissolved in a corn oil (90% by weight) to obtain an oral liquid formulation.

Formulation Example 24

Oral Paste Formulation

Aluminum distearate (5% by weight) is dispersed with heating into a mixture of a distilled palm oil (57% by weight) and polysorbate 85 (3% by weight). This mixture is cooled to room temperature, and saccharine (25% by weight) is dispersed into the oil vehicle. To the mixture is added the present hydrazide compound (1) (10% by weight) to obtain an oral paste formulation.

Formulation Example 25

Granules for Oral Administration

The present hydrazide compound (1) (5% by weight) is mixed with a lime stone powder (95% by weight), and the mixture is subjected to wet granulation to obtain granules for oral administration.

Formulation Example 26

Animal Feed Premix

The present hydrazide compound (1) (0.15% by weight), an animal feed (95% by weight), and, a mixture (4.85% by weight) of dicalcium phosphate, a diatom earth, Aerosil, and a carbonate (or chalk) are sufficiently stirred and mixed to obtain an animal feed premix.

Formulation Example 27

Animal Feed Premix

The present hydrazide compound (1) (0.15% by weight), Aerosil (2.5% by weight), a chalk (2.5% by weight), and an animal feed (94.85% by weight) are sufficiently stirred and mixed to obtain an animal feed premix.

Formulation Example 28

Liquid Formulation

The present hydrazide compound (1) (20 g) is dissolved in diethylene glycol monoethyl ether (80 g) to obtain a liquid formulation.

Formulation Example 29

Liquid Formulation

The present hydrazide compound (1) (20 g) is dissolved in propylene carbonate (80 g) to obtain a liquid formulation.

Formulation Example 30

Liquid Formulation

The present hydrazide compound (1) (20 g) is dissolved in diisopropyl adipate (80 g) to obtain a liquid formulation.

Formulation Example 31

Liquid Formulation

The present hydrazide compound (1) (20 g) is dissolved in diisobutyl adipate (80 g) to obtain a liquid formulation.

Formulation Example 32

Liquid Formulation

The present hydrazide compound (1) (20 g) is dissolved in γ-butyrolactone (80 g) to obtain a liquid formulation.

Formulation Example 33

Liquid Formulation

The present hydrazide compound (1) (20 g) is dissolved in a mixture of diethylene glycol monoethyl ether (40 g) and diisopropyl adipate (40 g) to obtain a liquid formulation.

Formulation Example 34

Liquid Formulation

The present hydrazide compound (1) (20 g) is dissolved in a mixture of silicone oil (10 g) and diethylene glycol monoethyl ether (70 g) to obtain a liquid formulation.

Formulation Example 35

Emulsifiable Concentrate

The present hydrazide compound (1) (5 g) is dissolved in a mixture of xylene (39.5 g) and N,N-dimethylformamide (39.5 g). To the mixture are added polyoxyethylene styryl phenyl ether (10 g) and calcium dodecylbenzenesulfonate (6 g), and the resulting mixture is stirred and mixed to obtain an emulsifiable concentrate.

Formulation Example 36

Shampoo

To the present hydrazide compound (1) (5 g) are added Nikkol TEALS-42 (manufactured by Nikko Chemicals Co., Ltd.; aqueous 42% triethanolamine lauryl sulfate solution; 60 g) and propylene glycol (20 g). The resulting mixture is sufficiently stirred and mixed to a homogeneous solution, and thereto is added water (19.5 g), and then the resulting mixture is sufficiently stirred and mixed to a shampoo as a homogeneous solution.

Formulation Example 37

Suppository

The present hydrazide compound (1) (7.2 g) and Hosco S-55 (manufactured by Maruishi Pharmaceutical Co., Ltd.; 92.8 g) are dissolved and mixed at 100° C., and the resulting mixture is poured into a mold for suppository, and cooled and solidified to a suppository.

Hereinafter, Test Examples supporting an excellent controlling effect of the controlling agent of the present invention on animal ectoparasites will be described. In some Test Examples, N'-{5-[5-(3,5-dichlorophenyl)-5-trifluoromethyl-4,5-dihydroisoxazol-3-yl]-2-chlorophenyl}acetohydrazide: Example 52 [hereinafter referred to as "Comparative compound (52)"] as described in WO2010/032437 (Applicant: Nippon Soda Co., Ltd.) was similarly tested as a comparative example, and the test results are also shown in the Test Examples.

Test Example 1

Pesticidal Activity on Ticks (*Haemaphysalis longicornis*) in Filter Paper Test The present hydrazide compound (5 mg) was dissolved in acetone (10 mL), and this acetone solution (1 mL) was uniformly applied onto one side of a filter paper (TOYO No. 2; 5×10 cm; the surface area of the filter paper was 50 cm$^2$, and thus the amount of the present hydrazide compound applied was 100 mg/m$^2$). After drying, said filter paper was folded, and the both sides of the paper were clipped to form a bag. Into this bag, test ticks (*Haemaphysalis longicornis*, non-blood-fed young ticks, 10 ticks/group) were added, and the opening was clipped to seal the bag. Two (2) days later, the number of dead ticks was examined and the mortality was calculated by the following formula:

Mortality (%)=100×(number of dead ticks/number of ticks tested)

As a result, the present hydrazide compound (1) showed a mortality of 90% or more.

Test Example 2

Dropping Application Against Mouse-Infested Ticks (*Haemaphysalis longicornis*)

The previous day before dropping application, 30 test ticks (*Haemaphysalis longicornis*, young ticks) were deposited on a mouse. Before the dropping application, uninfested ticks were removed.

The present hydrazide compound (1) (5 mg) was dissolved in a mixture (5 mL) of propylene carbonate and diethylene glycol monoethyl ether in equal amounts to prepare a 0.1% w/v solution. Said solution (200 μL) was applied dropwise to the whole body surface of a mouse with a pipette. To a control group, the mixture (200 μL) alone was applied. Each application was repeated 3 times per group.

Two (2) days after the application, the number of dead ticks was examined and the mortality was calculated by the following formula:

Mortality (%)=100×(number of dead ticks/infested ticks before dropping application)

As a result, the present hydrazide compound (1) showed a mortality of 70% or more.

Test Example 3

Oral Administration Against Mouse-Infested Ticks (*Haemaphysalis longicornis*)

The previous day before oral administration, 30 test ticks (*Haemaphysalis longicornis*, young ticks) were deposited on a mouse. Before the oral administration, uninfested ticks were removed.

The present hydrazide compound (1) (20 mg) was dissolved in dimethylformamide (680 mg), and thereto a corn oil was added to prepare a test solution (10 mL). Said test solution was orally administered to the mouse at the rate of 10 mL per 1 kg of the body weight of the mouse with a gastric sonde. To a control group, a 7% dimethylformamide/corn oil solution alone was orally administered. Each administration was repeated 3 times per group.

Two (2) days after the administration, the number of dead ticks was examined and the mortality was calculated by the following formula:

Mortality (%)=100×(number of dead ticks/infested ticks before oral administration)

As a result, the present hydrazide compound (1) showed a mortality of 90% or more.

Test Example 4

Dropping Application Against Dog-Infested Ticks (*Haemaphysalis longicornis*)

The previous day before dropping application, 100 test ticks (*Haemaphysalis longicornis*, young ticks) were deposited on a dog (beagle). Before the dropping application, infested ticks were counted.

Each (1.5 g) of the present hydrazide compound (1) and Comparative compound (52) was dissolved in diethylene glycol monoethyl ether (6.0 g) to prepare a test solution. Said test solution was directly dropped on the skin of the neck and back of the dog while pushing aside fur thereon at a rate of 0.1 ml per 1 kg of the dog's body weight (dose amount: 20 mg/kg). This is referred to as a test group. On the other hand, diethylene glycol monoethyl ether alone was applied dropwise to a placebo group.

Two (2) days after the application, the number of living ticks, which were infesting the dogs, was examined. When the examination was completed, all infested ticks were removed from the dogs.

The infestation rate and control rate were calculated by the following formulae:

Method of calculating infestation rate and control rate at the initial stage (2 days) after the application:

Infestation rate (%) at X days after application=(number of living ticks at X days/number of living ticks before application)×100

Control rate (%) at X days after application=(infestation rate of test group before application−infestation rate of test group at X days)/infestation rate of test group before application×100

In addition, if an infestation rate of a test group is higher than a placebo group, then the control rate is deemed to be 0%.

As a result, the present hydrazide compound (1) showed excellent tick control activities at a dose of 20 mg/kg at 2 days after the application (Table 1).

TABLE 1

| | Tick control rates (%) at 2 days after the application |
|---|---|
| Compound (1) | 94 |
| Comparative compound (52) | 44 |

INDUSTRIAL APPLICABILITY

The controlling agent of the present invention has an excellent controlling effect on animal ectoparasites, and thus is useful for controlling animal ectoparasites.

What is claimed is:

1. An animal ectoparasite-controlling agent comprising a hydrazide compound represented by the formula (1):

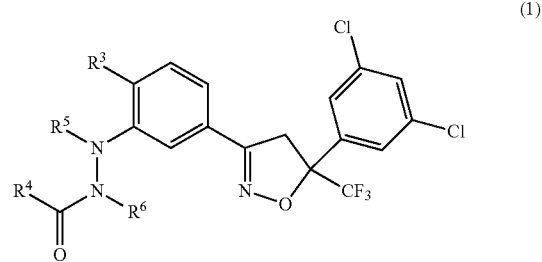

(1)

wherein $R^3$ represents a fluorine atom, a chlorine atom, a bromine atom, a methyl group, an ethyl group or a hydrogen atom, $R^5$ and $R^6$ are the same or different from each other and each represents a methyl group or a hydrogen atom, and $R^4$ represents a C1-C6 alkyl group substituted by a C1-C6 alkoxy group, as an active ingredient.

2. The animal ectoparasite-controlling agent according to claim 1, wherein in the formula (1) $R^6$ is a hydrogen atom.

3. The animal ectoparasite-controlling agent according to claim 1 or 2, wherein in the formula (1) $R^3$ is a chlorine atom.

4. The animal ectoparasite-controlling agent according to claim 1, wherein in the formula (1) $R^5$ is a hydrogen atom.

5. The animal ectoparasite-controlling agent according to claim 1, wherein in the formula (1) $R^5$ is a methyl group.

6. The animal ectoparasite-controlling agent according to claim 1, which is in the form of an oral formulation or an external formulation for skin.

7. The animal ectoparasite-controlling agent according to claim 1, which is in the form of a liquid formulation.

8. The animal ectoparasite-controlling agent according to claim 1, which is in the form of a capsule formulation, a tablet or a chewable tablet.

9. The animal ectoparasite-controlling agent according to claim 1, wherein the animal ectoparasite is a flea or a tick.

10. A method for controlling an animal ectoparasite, which comprises applying an effective amount of a hydrazide compound of the formula (1):

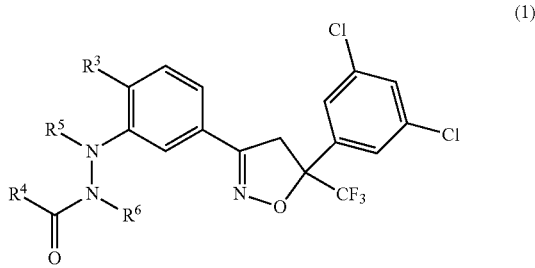

wherein $R^3$ represents a fluorine atom, a chlorine atom, a bromine atom, a methyl group, an ethyl group or a hydrogen atom, $R^5$ and $R^6$ are the same or different from each other and each represents a methyl group or a hydrogen atom, and $R^4$ represents a C1-C6 alkyl group substituted by a C1-C6 alkoxy group, to an animal.

11. The method for controlling an animal ectoparasite according to claim 10, wherein the hydrazide compound is orally administered.

12. The method for controlling an animal ectoparasite according to claim 10, wherein the hydrazide compound is externally applied to a skin.

13. The method for controlling an animal ectoparasite according to claim 12, wherein the hydrazide compound is applied by spot-on application or pour-on application.

14. The method for controlling an animal ectoparasite according to any one of claims 10 to 13, wherein the animal is a dog or a cat.

15. The method for controlling an animal ectoparasite according to any one of claims 10 to 13, wherein the animal is a cow, a horse, a pig or a sheep.

16. The method for controlling an animal ectoparasite according to claim 10, wherein the animal ectoparasite is a flea or a tick.

* * * * *